US012624367B2

(12) United States Patent
Agbandje-McKenna et al.

(10) Patent No.: US 12,624,367 B2
(45) Date of Patent: May 12, 2026

(54) AAV6 VARIANTS

(71) Applicant: University of Florida Research Foundation, Incorporated, Gainesville, FL (US)

(72) Inventors: Mavis Agbandje-McKenna, Gainesville, FL (US); Antonette D. Bennett, Gainesville, FL (US); Robert McKenna, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 1037 days.

(21) Appl. No.: 17/042,865

(22) PCT Filed: Mar. 29, 2019

(86) PCT No.: PCT/US2019/025045
§ 371 (c)(1),
(2) Date: Sep. 28, 2020

(87) PCT Pub. No.: WO2019/191716
PCT Pub. Date: Oct. 3, 2019

(65) Prior Publication Data
US 2021/0017542 A1     Jan. 21, 2021

Related U.S. Application Data

(60) Provisional application No. 62/650,213, filed on Mar. 29, 2018.

(51) Int. Cl.
| | |
|---|---|
| *C12N 15/86* | (2006.01) |
| *A61K 35/76* | (2015.01) |
| *A61K 48/00* | (2006.01) |
| *C12N 7/00* | (2006.01) |
| *G01N 33/68* | (2006.01) |

(52) U.S. Cl.
CPC .......... *C12N 15/86* (2013.01); *A61K 48/0075* (2013.01); *C12N 7/00* (2013.01); *G01N 33/6854* (2013.01); *A61K 35/76* (2013.01); *A61K 48/00* (2013.01); *C12N 2750/14122* (2013.01); *C12N 2750/14123* (2013.01); *C12N 2750/14143* (2013.01); *C12N 2750/14151* (2013.01)

(58) Field of Classification Search
CPC .... A61K 48/00; A61K 48/0075; A61K 35/76; C12N 15/86; C12N 7/00; C12N 2750/14122; C12N 2750/14123; C12N 2750/14143; C12N 2750/14151; C12N 2710/14144; G01N 33/6854
USPC ....... 424/199.1, 233.1; 514/44 R; 435/320.1, 435/7.1
See application file for complete search history.

(56) References Cited

U.S. PATENT DOCUMENTS

| | | | | |
|---|---|---|---|---|
| 2013/0189225 | A1* | 7/2013 | Voit ....................... | A61K 38/21 |
| | | | | 424/85.4 |
| 2021/0032660 | A1 | 2/2021 | Samulski et al. | |

FOREIGN PATENT DOCUMENTS

| | | | |
|---|---|---|---|
| ES | 2629087 | * | 8/2017 |
| WO | WO 2017/058892 A2 | | 4/2017 |
| WO | WO 2017/106236 A1 | | 6/2017 |
| WO | WO 2019/191418 A1 | | 10/2019 |

OTHER PUBLICATIONS

Gurda et al. (2013) J. Virol., vol. 87(16), 9111-9124.*
Basner-Tschakarjan et al. (2014) Front. Immunol., vol. 5, 1-5.*
Kuck et al. (2007) J. Vir. Meth., vol. 140, 17-24.*
Zaiss et al. (2008) Gene Therapy, vol. 15, 808-816.*
English Translation of ES 2629087 (Aug. 7, 2017) Arbetman et al., pp. 1-59.*
Pommie et al. (2004) J. Mol. Recognition, vol. 17, 17-32.*
Vance et al. (2015) AAV Biology, Infectivity and Therapeutic Use from Bench to Clinic, Chapter 5, dx.doi.org/10.5772/61988, pp. 119-143.*
International Search Report and Written Opinion mailed Jul. 10, 2019 in connection with Application No. PCT/US2019/025045.
International Preliminary Report on Patentability mailed Oct. 8, 2020 in connection with Application No. PCT/US2019/025045.
Extended European Search Report for EP Application No. 19775778.4, mailed Dec. 20, 2021.
Bennett et al., 91. AAV6 K531 Serves a Dual Function in Selective Receptor and Antibody ADK6 Recognition. Molecular Therapy. May 2017;25(5S1):44.
Bennett et al., AAV6 K531 serves a dual function in selective receptor and antibody ADK6 recognition. Virology. May 2018:518:369-376. doi: 10.1016/j.virol.2018.03.007. Epub Mar. 30, 2018.
Boutin et al., Prevalence of serum IgG and neutralizing factors against adeno-associated virus (AAV) types 1, 2, 5, 6, 8, and 9 in the healthy population: implications for gene therapy using AAV vectors. Hum Gene Ther. Jun. 2010;21(6):704-12. doi: 10.1089/hum.2009.182.
Buller et al., Characterization of adenovirus-associated virus-induced polypeptides in KB cells. J Virol. Jan. 1978;25(1):331-8. doi: 10.1128/JVI.25.1.331-338.1978.
Büning et al., Progress in the use of adeno-associated viral vectors for gene therapy. Cells Tissues Organs. 2004;177(3):139-50. doi: 10.1159/000079988.
Carrillo-Tripp et al., VIPERdb2: an enhanced and web API enabled relational database for structural virology. Nucleic Acids Res. Jan. 2009;37:D436-42. doi: 10.1093/nar/gkn840. Epub Nov. 3, 2008.

(Continued)

*Primary Examiner* — Anne Marie S Wehbe
(74) *Attorney, Agent, or Firm* — Wolf, Greenfield & Sacks, P.C.

(57)          ABSTRACT

This disclosure relates to variant AAV6 particles engineered to escape host neutralizing antibodies but retain or improve transduction efficiency, and their use as gene delivery vehicles.

19 Claims, 8 Drawing Sheets

Specification includes a Sequence Listing.

(56)        References Cited

OTHER PUBLICATIONS

Dimattia et al., Production, purification, crystallization and preliminary X-ray structural studies of adeno-associated virus serotype 5. Acta Crystallogr Sect F Struct Biol Cryst Commun. Oct. 1, 2005;61(Pt 10):917-21. doi: 10.1107/S1744309105028514. Epub Sep. 30, 2005.

Emsley et al., Features and development of Coot. Acta Crystallogr D Biol Crystallogr. Apr. 2010;66(Pt 4):486-501. doi: 10.1107/S0907444910007493. Epub Mar. 24, 2010.

Gao et al., Clades of Adeno-associated viruses are widely disseminated in human tissues. J Virol. Jun. 2004;78(12):6381-8. doi: 10.1128/JVI.78.12.6381-6388.2004.

Gao et al., Novel adeno-associated viruses from rhesus monkeys as vectors for human gene therapy. Proc Natl Acad Sci U S A. Sep. 3, 2002;99(18):11854-9. doi: 10.1073/pnas.182412299. Epub Aug. 21, 2002.

Gaudet et al., Gene therapy for lipoprotein lipase deficiency. Curr Opin Lipidol. Aug. 2012;23(4):310-20. doi: 10.1097/MOL. 0b013e3283555a7e.

Gurda et al., Mapping a neutralizing epitope onto the capsid of adeno-associated virus serotype 8. J Virol. Aug. 2012;86(15):7739-51. doi: 10.1128/JVI.00218-12. Epub May 16, 2012.

Huang et al., AAV2 production with optimized N/P ratio and PEI-mediated transfection results in low toxicity and high titer for in vitro and in vivo applications. J Virol Methods. Nov. 2013;193(2):270-7. doi: 10.1016/j.jviromet.2013.06.008. Epub Jun. 19, 2013. Author manuscript, 18 pages.

Huang et al., Characterization of the Adeno-Associated Virus 1 and 6 Sialic Acid Binding Site. J Virol. May 12, 2016;90(11):5219-5230. doi: 10.1128/JVI.00161-16. Print Jun. 1, 2016.

Hurlbut et al., Preexisting immunity and low expression in primates highlight translational challenges for liver-directed AAV8-mediated gene therapy. Mol Ther. Nov. 2010;18(11):1983- 94. doi: 10.1038/mt.2010.175. Epub Aug. 24, 2010.

Huttner et al., Genetic modifications of the adeno-associated virus type 2 capsid reduce the affinity and the neutralizing effects of human serum antibodies. Gene Ther. Dec. 2003;10(26):2139-47. doi: 10.1038/sj.gt.3302123. Author manuscript, 22 pages.

Kotterman et al., Engineering adeno-associated viruses for clinical gene therapy. Nat Rev Genet. Jul. 2014;15(7):445-51. doi: 10.1038/nrg3742. Epub May 20, 2014. Author manuscript, 18 pages.

Krissinel et al., Inference of macromolecular assemblies from crystalline state. J Mol Biol. Sep. 21, 2007;372(3):774-97. doi: 10.1016/j.jmb.2007.05.022. Epub May 13, 2007.

Kuck et al., Development of AAV serotype-specific ELISAs using novel monoclonal antibodies. J Virol Methods. Mar. 2007;140(1-2):17-24. doi: 10.1016/j.jviromet.2006.10.005. Epub Nov. 28, 2006.

Li et al., Neutralizing antibodies against adeno-associated virus examined prospectively in pediatric patients with hemophilia. Gene Ther. Mar. 2012;19(3):288-94. doi: 10.1038/gt.2011.90. Epub Jun. 23, 2011.

Li et al., Single amino acid modification of adeno-associated virus capsid changes transduction and humoral immune profiles. J Virol. Aug. 2012;86(15):7752-9. doi: 10.1128/JVI.00675-12. Epub May 16, 2012.

Limberis et al., Transduction efficiencies of novel AAV vectors in mouse airway epithelium in vivo and human ciliated airway epithelium in vitro. Mol Ther. Feb. 2009;17(2):294-301. doi: 10.1038/mt.2008.261. Epub Dec. 9, 2008.

Lisowski et al., Selection and evaluation of clinically relevant AAV variants in a xenograft liver model. Nature. Feb. 20, 2014;506(7488):382-6. doi: 10.1038/nature12875. Epub Dec. 25, 2013. Author manuscript, 19 pages.

Lochrie et al., Mutations on the external surfaces of adeno-associated virus type 2 capsids that affect transduction and neutralization. J Virol. Jan. 2006;80(2):821-34. doi: 10.1128/JVI.80.2.821-834.2006.

Manno et al., Successful transduction of liver in hemophilia by AAV-Factor IX and limitations imposed by the host immune response. Nat Med. Mar. 2006;12(3):342-7. doi: 10.1038/nm1358. Epub Feb. 12, 2006.

Mccraw et al., Structure of adeno-associated virus-2 in complex with neutralizing monoclonal antibody A20. Virology. Sep. 2012;431(1-2):40-9. doi: 10.1016/j.virol.2012.05.004. Epub Jun. 9, 2012.

Mendell et al., LGMD 2D gene therapy restores alpha-sarcoglycan and associated proteins. Ann Neurol. Sep. 2009;66(3):290-7. doi: 10.1002/ana.21732. Author manuscript, 15 pages.

Mietzsch et al., OneBac: platform for scalable and high-titer production of adeno-associated virus serotype 1-12 vectors for gene therapy. Hum Gene Ther. Mar. 2014;25(3):212-22. doi: 10.1089/hum.2013.184. Epub Jan. 23, 2014.

Miller et al., Production, purification and preliminary X-ray crystallographic studies of adeno-associated virus serotype 1. Acta Crystallogr Sect F Struct Biol Cryst Commun. Dec. 1, 2006;62(Pt 12):1271-4. doi: 10.1107/S1744309106048184. Epub Nov. 30, 2006.

Mindell et al., Accurate determination of local defocus and specimen tilt in electron microscopy. J Struct Biol. Jun. 2003;142(3):334-47. doi: 10.1016/s1047-8477(03)00069-8.

Mori et al., Tissue distribution of cynomolgus adeno-associated viruses AAV10, AAV11, and AAVcy.7 in naturally infected monkeys. Arch Virol. 2008;153(2):375-80. doi: 10.1007/s00705-007-1097-8. Epub Dec. 10, 2007.

Nance et al., Perspective on Adeno-Associated Virus Capsid Modification for Duchenne Muscular Dystrophy Gene Therapy. Hum Gene Ther. Dec. 2015;26(12):786-800. doi: 10.1089/hum.2015.107. Epub Oct. 15, 2015.

Nathwani et al., Adenovirus-associated virus vector-mediated gene transfer in hemophilia B. N Engl J Med. Dec. 22, 2011;365(25):2357-65. doi: 10.1056/NEJMoa1108046. Epub Dec. 10, 2011.

Ng et al., Structural Characterization of the Dual Glycan Binding Adeno-Associated Virus Serotype 6. J Virol. Dec. 2010; 84(24): 12945-12957. Published online Sep. 22, 2010. doi: 10.1128/JVI. 01235-10.

Pettersen et al., UCSF Chimera—a visualization system for exploratory research and analysis. J Comput Chem. Oct. 2004;25(13):1605-12. doi: 10.1002/jcc.20084.

Rose et al., Structural Proteins of Adenovirus-Associated Viruses. J Virol. Nov. 1971;8(5): 766-770. doi: 10.1128/jvi.8.5.766-770.1971.

Schmidt et al., Adeno-associated virus type 12 (AAV12): a novel AAV serotype with sialic acid- and heparan sulfate proteoglycan-independent transduction activity. J Virol. Feb. 2008;82(3):1399-406. doi: 10.1128/JVI.02012-07. Epub Nov. 28, 2007.

Snijder et al., Defining the stoichiometry and cargo load of viral and bacterial nanoparticles by Orbitrap mass spectrometry. J Am Chem Soc. May 21, 2014;136(20):7295-9. doi: 10.1021/ja502616y. Epub May 7, 2014.

Sonntag et al., The assembly-activating protein promotes capsid assembly of different adeno-associated virus serotypes. J Virol. Dec. 2011;85(23):12686-97. doi: 10.1128/JVI.05359-11. Epub Sep. 14, 2011.

Tse et al., Structure-guided evolution of antigenically distinct adeno-associated virus variants for immune evasion. Proc Natl Acad Sci U S A. Jun. 13, 2017;114(24):E4812-E4821. doi: 10.1073/pnas. 1704766114. Epub May 2017.

Tseng et al., Adeno-associated virus serotype 1 (AAV1)- and AAV5-antibody complex structures reveal evolutionary commonalities in parvovirus antigenic reactivity. J Virol. Feb. 2015;89(3):1794-808. doi: 10.1128/JVI.02710-14. Epub Nov. 19, 2014.

Tseng et al., Generation and characterization of anti-Adeno-associated virus serotype 8 (AAV8) and anti-AAV9 monoclonal antibodies. J Virol Methods. Oct. 2016:236:105-110. doi: 10.1016/j.jviromet.2016.07.009. Epub Jul. 14, 2016. Author manuscript, 14 pages.

Tseng et al., Mapping the AAV Capsid Host Antibody Response toward the Development of Second Generation Gene Delivery Vectors. Front Immunol. Jan. 30, 2014:5:9. doi: 10.3389/fimmu. 2014.00009. eCollection 2014.

Van Heel et al., Fourier shell correlation threshold criteria. J Struct Biol. Sep. 2005;151(3):250-62. doi: 10.1016/j.jsb.2005.05.009.

(56) References Cited

OTHER PUBLICATIONS

Wagner et al., Safety and biological efficacy of an adeno-associated virus vector-cystic fibrosis transmembrane regulator (AAV-CFTR) in the cystic fibrosis maxillary sinus. Laryngoscope. Feb. 1999;109(2 Pt 1):266-74. doi: 10.1097/00005537-199902000-00017.

Wobus et al., Monoclonal antibodies against the adeno-associated virus type 2 (AAV-2) capsid: epitope mapping and identification of capsid domains involved in AAV-2-cell interaction and neutralization of AAV-2 infection. J Virol. Oct. 2000;74(19):9281-93. doi: 10.1128/jvi.74.19.9281-9293.2000.

Wu et al., Single amino acid changes can influence titer, heparin binding, and tissue tropism in different adeno-associated virus serotypes. J Virol. Nov. 2006;80(22):11393-7. doi: 10.1128/JVI.01288-06. Epub Aug. 30, 2006.

Xiao et al., Interpretation of Electron Density with Stereographic Roadmap Projections. J Struct Biol. May 2007; 158(2): 182-187. Published online Oct. 24, 2006. doi: 10.1016/j.jsb.2006.10.013. Author manuscript, 12 pages.

Yan et al., Ab initio random model method facilitates 3D reconstruction of icosahedral particles. J Struct Biol. Jan. 2007;157(1):211-25. doi: 10.1016/j.jsb.2006.07.013. Epub Aug. 11, 2006. Author manuscript, 27 pages.

Yan et al., AUTO3DEM—an automated and high throughput program for image reconstruction of icosahedral particles. J Struct Biol. Jan. 2007;157(1):73-82. doi: 10.1016/j.jsb.2006.08.007. Epub Aug. 25, 2006. Author manuscript, 18 pages.

Zadori et al., A viral phospholipase A2 is required for parvovirus infectivity. Dev Cell. Aug. 2001;1(2):291-302. doi: 10.1016/s1534-5807(01)00031-4.

Zolotukhin et al., Production and purification of serotype 1, 2, and 5 recombinant adeno-associated viral vectors. Methods. Oct. 2002;28(2):158-67. doi: 10.1016/s1046-2023(02)00220-7.

Li et al., The different interactions of lysine and arginine side chains with lipid membranes. J Phys Chem B. Oct. 10, 2013;117(40):11906-20. doi: 10.1021/jp405418y. Epub Sep. 27, 2013. Author Manuscript, 38 pages.

* cited by examiner

Contact residues – S264, G266, N269, H272, Q457, S588, and T589

Occluded residues – 262-272, 382-386, 445-457, 459, 469-473, 488-489, 494-496, 499-515, 528-534, 571-579, 584-589 and 593-595

K531  L584

| RESIDUE No | 531 | 584 | 598 | 642 |
|---|---|---|---|---|
| AAV1 | E | F | A | N |
| AAV6 | K | L | V | H |
FIG. 2A
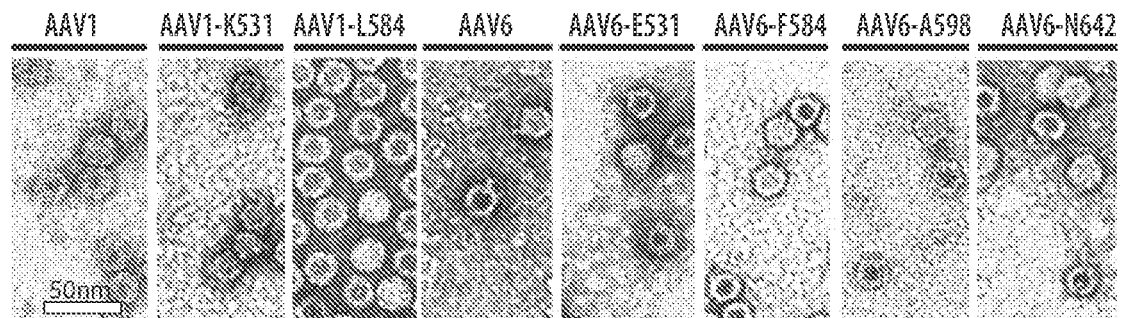
AAV1    AAV1-K531    AAV1-L584    AAV6    AAV6-E531    AAV6-F584    AAV6-A598    AAV6-N642
50nm
FIG. 2B
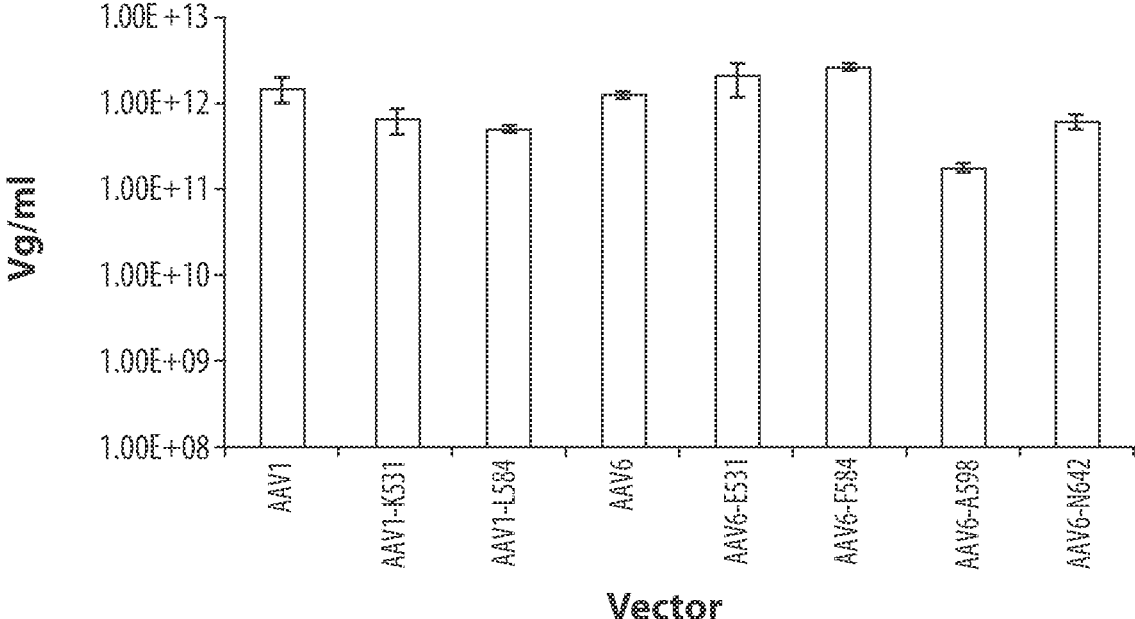
FIG. 2C

Molar Ratio of ADK6: Vector

$\dots\dots\overset{1}{\dots}$ AAV6        $\overset{3}{\rule{1cm}{0.4mm}}$ AAV6-E531        $\overset{5}{\text{--}\cdot\text{--}}$ AAV6-F584

$\overset{2}{\cdot\text{--}\cdot\text{--}}$ AAV6-A598        $\dots\overset{4}{\dots}$ AAV6-642

Contact residues - S264, G266, N269, H272, Q457, S588, and T589

Occluded residues - 262-272, 382-386, 445-457, 459, 469-473, 488-489, 494-496, 499-515, 528-534, 571-579, 584-589 and 593-595

Basic receptor residues - K459, K493, K531, and R576

Polar receptor residues - N447, S472, N500, and T502

Hydrophobic receptor residues - V473 and W503

AAV6 VARIANTS

RELATED APPLICATIONS

This application is national stage filing under 35 U.S.C. § 371 of international application number PCT/US2019/025045, filed Mar. 29, 2019, which claims the benefit of U.S. provisional application No. 62/650,213, filed Mar. 29, 2018, each of which is incorporated herein by reference in its entirety.

GOVERNMENT SUPPORT

This invention was made with government support under R01 GM082946 awarded by the National Institutes of Health. The government has certain rights in the invention.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Sep. 28, 2020, is named U119670054US01-SEQ-PRW.txt, and is 71 bytes in size.

BACKGROUND

Adeno-associated virus (AAV) of serotype 6 are being developed as vectors for the treatment of various diseases, disorders, and conditions, especially those targeting the lung and skeletal muscle. However, pre-existing antibodies for AAV6 present a significant limitation to achieving optimal efficacy for the AAV6 gene delivery system.

SUMMARY

The present disclosure is based, at least in part, on the identification of an AAV6 capsid residue that is important for interactions with antibodies that recognize AAV6 capsids and which would result in reduced transduction and gene expression in target cells when AAV6 particles are administered to a subject. The inventors of this disclosure identified amino acid K531 (VP1 numbering) common to all three capsid proteins Vp1, VP2, and VP3, as a determinant of monoclonal antibody ADK6 recognition of AAV6 by determining the structure of AAV6-ADK6 complex using cyroelectron microscopy (cryo-EM). The footprint of the interaction between AAV6 and ADK6 was also confirmed by cell-based assays. Using this footprint, the inventors of the present disclosure developed rAAV particles with substituted amino acids residues in this footprint (e.g., at residue K531) that are able to evade neutralizing antibodies when administered to subjects. One advantage of an neutralizing antibody-evading AAV particle is that fewer particles are needed to be administered to a subject for delivering a gene compared to an AAV particle that do not evade neutralizing antibodies.

Accordingly, the present disclosure provides a method with which to deliver one or more genes of interest to target cells of a subject in which it is anticipated that AAV particles used to comprise and deliver the one or more genes of interest will be recognized by neutralizing antibodies. In some aspects, provided herein is a method comprising administering to a subject that is seropositive for AAV6 a recombinant rAAV6 particle that is able to evade anti-AAV6 antibodies. In some embodiments, a variant recombinant rAAV6 particle that is able to evade anti-AAV6 antibodies comprises a capsid protein comprising a substituted amino acid at position 531, and the rAAV particle comprises a gene of interest.

In some embodiments, the subject has preexisting anti-AAV6 antibodies. In some embodiments, a method of administering to a subject a rAAV6 particle comprising a substitution at position 531K of one or more of its capsid proteins further comprises determining whether the subject is seropositive for AAV6.

In some embodiments, determining whether the subject is seropositive for AAV6 comprises determining whether a subject has anti-AAV6 antibodies. In some embodiments, determining whether a subject has anti-AAV6 antibodies comprises incubating a sample of serum obtained from the subject with one or more AAV6 capsid antigens, and measuring the amount of anti-AAV6 antibodies bound to the one or more AAV6 capsid antigens. In some embodiments, the one or more AAV6 capsid antigens are bound to a solid support. In some embodiments, the antibodies in a subjects serum sample are bound to a solid support. In some embodiments, AAV6 capsid antigens is a protein or peptide. In some embodiments, proteins or peptides that are AAV6 capsid antigens have a sequence that is comprised in AAV6 VP1, VP2, or VP3 capsid proteins.

In some embodiments, a variant rAAV6 particle as disclosed herein comprises a capsid protein comprising amino acid sequence of a serotype other than serotype 6. In some embodiments, the substituted amino acid at position 531 is glutamic acid, aspartic acid, histidine, tyrosine, arginine, methionine, or leucine. In some embodiments, the substituted amino acid at position 531 is glutamic acid, aspartic acid, histidine, tyrosine, or arginine. In some embodiments, the substituted amino acids at position 531 of a variant rAAV6 particle is negatively charged. In some embodiments, the substituted amino acids at position 531 of a variant rAAV6 particle that is negatively charged is glutamic acid or aspartic acid. In some embodiments, the subject was previously exposed to a rAAV particle. In some embodiments, a subject had been previously administered a rAAV particle. In some embodiments, a particle to which a subject was previously exposed or had been previously administered is of serotype 6. In some embodiments, a subject is human.

In some embodiments, the gene of interest that is comprised by any one of the variant rAAV6 particles disclosed herein that is delivered using any one of the methods described herein encodes a therapeutic protein. In some embodiments, a gene of interest encodes an antibody, a peptibody, a growth factor, a clotting factor, a hormone, a membrane protein, a cytokine, a chemokine, an activating or inhibitory peptide acting on cell surface receptors or ion channels, a cell-permeant peptide targeting intracellular processes, a thrombolytic, an enzyme, a bone morphogenetic protein, a differentiation factor, a nuclease or other protein used for gene editing, an Fc-fusion protein, an anticoagulant, a nuclease, guide RNA or other nucleic acid or protein for gene editing.

In some embodiments any one of the variant rAAV particles disclosed herein is administered to a subject subcutaneously, intraocularly, intravitreally, subretinally, parenterally, intravenously (IV), intracerebro-ventricularly, intramuscularly, intrathecally (IT), intracisternally, orally, intraperitoneally, by oral or nasal inhalation, or by direct injection to one or more cells, tissues, or organs by direct injection.

In some aspects, provided herein is a method comprising administering to a subject a subsequent rAAV6 particle, wherein the subsequent rAAV6 particle comprises a capsid protein comprising a substituted amino acid at position 531, wherein the rAAV particle comprises a gene of interest, and wherein the subject had previously received a rAAV particle. In some embodiments, a previously received rAAV particle is of serotype 6.

In some embodiments, a subsequent rAAV6 particle is administered within 12 months of the previously received rAAV particle. In some embodiments, a subject that is administered a subsequent rAAV6 particle is seropositive for AAV6. In some embodiments, a subject that is administered a subsequent rAAV6 particle has preexisting anti-AAV6 antibodies.

In some embodiments, a method comprising administering a subsequent rAAV6 particle to a subject further comprises determining whether the subject is seropositive for anti-AAV6 antibodies. In some embodiments, determining whether the subject is seropositive for AAV6 comprises determining whether a subject has anti-AAV6. In some embodiments, determining whether the subject has anti-AAV6 antibodies comprises incubating a sample of serum obtained from the subject with one or more AAV6 capsid antigens, and measuring the amount of anti-AAV6 antibodies bound to the one or more AAV6 capsid antigens. In some embodiments, the one or more AAV6 capsid antigens are bound to a solid support. In some embodiments, the antibodies in a subjects serum sample are bound to a solid support. In some embodiments, AAV6 capsid antigens is a protein or peptide. In some embodiments, proteins or peptides that are AAV6 capsid antigens have a sequence that is comprised in AAV6 VP1, VP2, or VP3 capsid proteins.

In some embodiments, a subsequent variant rAAV6 particle as disclosed herein comprises a capsid protein comprising amino acid sequence of a serotype other than serotype 6. In some embodiments, the substituted amino acid at position 531 is glutamic acid, aspartic acid, histidine, tyrosine, arginine, methionine, or leucine. In some embodiments, the substituted amino acid at position 531 is glutamic acid, aspartic acid, histidine, tyrosine, or arginine. In some embodiments, the substituted amino acids at position 531 of a subsequent variant rAAV6 particle is negatively charged. In some embodiments, the substituted amino acids at position 531 of a subsequent variant rAAV6 particle that is negatively charged is glutamic acid or aspartic acid. In some embodiments, the subject was previously exposed to a rAAV particle. In some embodiments, a subject had been previously administered a rAAV particle. In some embodiments, a particle to which a subject was previously exposed or had been previously administered is of serotype 6. In some embodiments, a subject is human.

In some embodiments, the gene of interest that is comprised by any one of the variant rAAV6 particles disclosed herein that is delivered using any one of the methods described herein encodes a therapeutic protein. In some embodiments, a gene of interest encodes an antibody, a peptibody, a growth factor, a clotting factor, a hormone, a membrane protein, a cytokine, a chemokine, an activating or inhibitory peptide acting on cell surface receptors or ion channels, a cell-permeant peptide targeting intracellular processes, a thrombolytic, an enzyme, a bone morphogenetic protein, a differentiation factor, a nuclease or other protein used for gene editing, an Fc-fusion protein, an anticoagulant, a nuclease, guide RNA or other nucleic acid or protein for gene editing.

In some embodiments any one of the variant rAAV particles disclosed herein is administered to a subject subcutaneously, intraocularly, intravitreally, subretinally, parenterally, intravenously (IV), intracerebro-ventricularly, intramuscularly, intrathecally (IT), intracisternally, orally, intraperitoneally, by oral or nasal inhalation, or by direct injection to one or more cells, tissues, or organs by direct injection.

In some aspects, provided herein is a method of identifying a footprint of interaction between an antibody and an rAAV6 particle, the method comprising contacting the antibody to the capsid under cryo-EM conditions, imaging using EM, and performing analysis on the image to identify points of contact between the antibody and the rAAV6 particle.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. It is to be understood that the data illustrated in the drawings in no way limit the scope of the disclosure.

FIG. 1A shows a surface density representation of the cryo-reconstructed AAV6-ADK6 Fab complex structure viewed along the icosahedral 2-fold axis. The capsid density is shown in light gray and the Fab is shown in light dark gray. The panel on the right shows a zoomed in image of the complex density map and docked pseudo-atomic model with contact residues with arrows. FIG. 1B shows AAV6 capsid surface with Fab contact residues in dark gray (as shown by the label), occluded residues in medium gray (as shown by the label), and K531 and L584, within the occluded region, in black (basic) and white (hydrophobic), respectively. The viral asymmetric unit, bounded by a 5-fold and two 3-fold axes intercepted by a 2-fold axis, is depicted by a large black triangle. The 2-, 3-, and 5-fold axes are represented by an oval, triangle, and pentagon, respectively. FIG. 1C shows a 2D "roadmap" projection of the residues within a viral asymmetric unit. Images in FIGS. 1A-C were generated by the Chimera (Pettersen et al., 2004, J Comput Chem 25, 1605-1612.), PyMol (Schrödinger 2017), and RIVEM programs (Xiao and Rossmann, 2007, J Struct Biol 158, 182-187) for FIG. 1A, FIG. 1B, and FIG. 1C, respectively.

FIGS. 2A-2C show data confirming proper production and purification of wild-type and variant AAV1 and AAV6 particles. FIG. 2A shows residue positions and type for surface amino acids plus internal residue 642 which differ between AAV1 and AAV6. FIG. 2B shows negative stained EM of wild-type and variant AAV1 and AAV6 particles. The scale bar is shown in white on the first EM image. FIG. 2C shows quantitation of purified particle genome titer determined by qPCR for wild-type and variant AAV1 and AAV6 particles.

FIG. 3A shows an immunoblot of denatured wild-type and variant AAV1 and AAV6 particles detected by B1 (which recognizes a linear epitope of the C-terminus of the VP1/2/3 common region) (top) and by ADK6 (which recognizes native capsids). ADK6 interacts specifically with AAV6, and this interaction is lost in mutant AAV6-E531 and restored in AAV1-K531. FIG. 3B shows data from neutralization assays for wild-type and variants of AAV1 in the presence of ADK6. FIG. 3C shows data from neutralization assays for wild-type and variants of AAV6 in the presence of ADK6. Transduction is normalized to the luciferase signal for wild-type virus at zero antibody concentration.

Figure 4A:
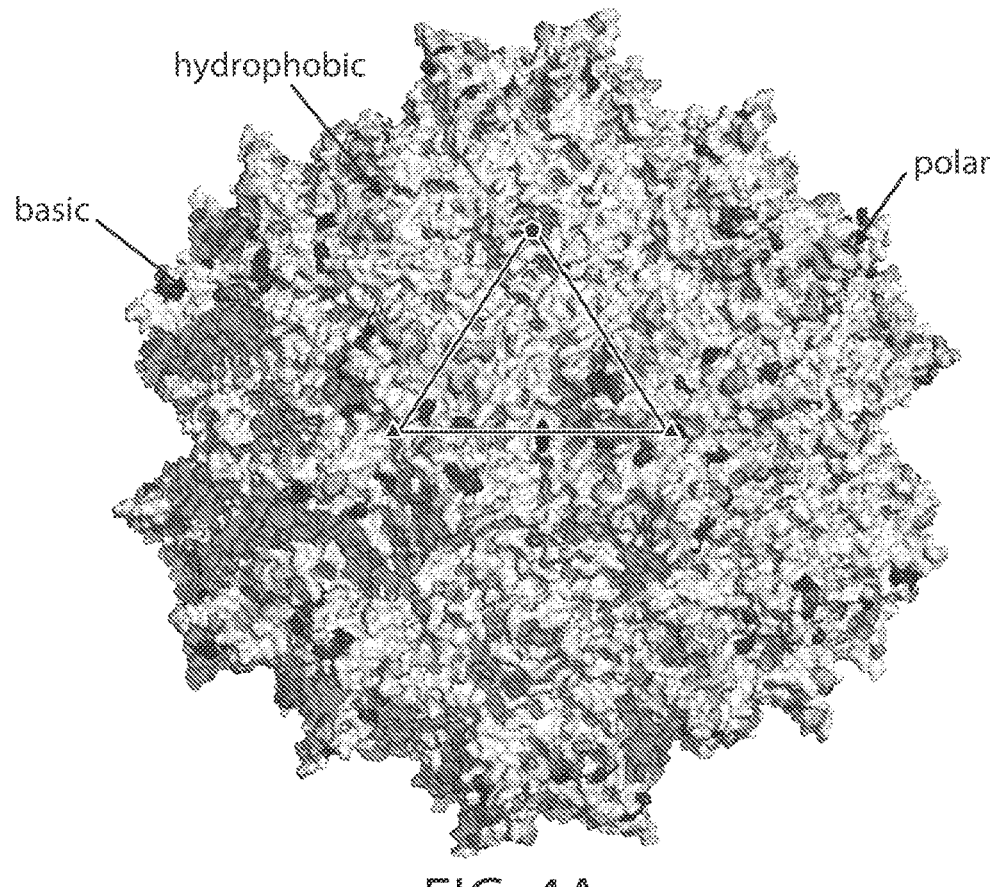
Figure 4B:
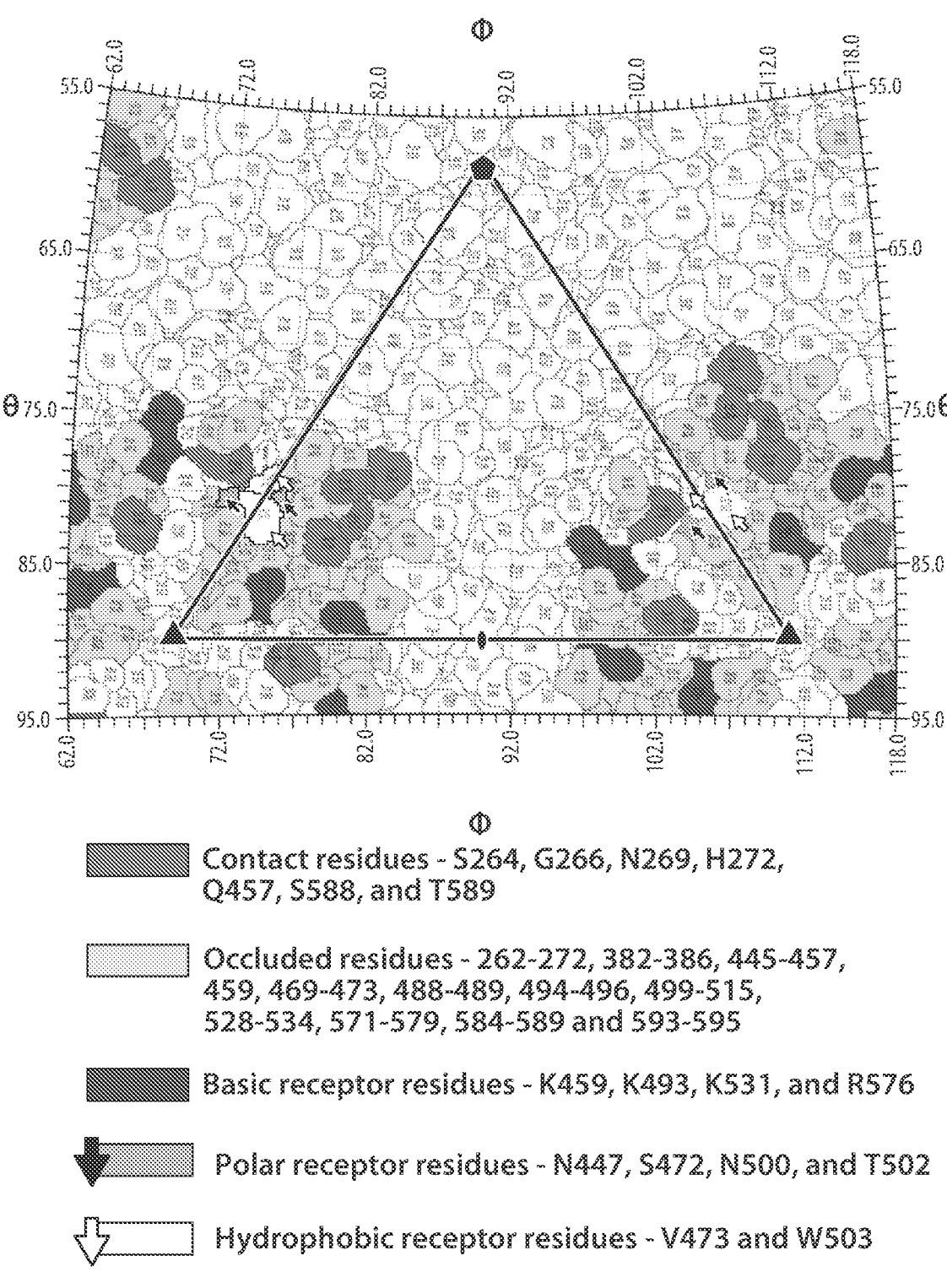

FIGS. 4A-4B show the functional surface of AAV6. FIG. 4A shows the capsid surface. FIG. 4B shows a 2D roadmap projection of AAV6, shaded as in FIGS. 1A-1C. SIA and HS receptor binding residues are colored black, medium-dark gray, and white (as shown by the labels) for basic, polar, and hydrophobic residues, respectively. The viral asymmetric unit are depicted as in FIGS. 1A-1C. The images for FIG. 4A and FIG. 4B were generated in the PyMol (Schrödinger, 2017) and RIVEM programs (Xiao and Rossmann, 2007, J Struct Biol 158, 182-187), respectively.

Figure 5A:
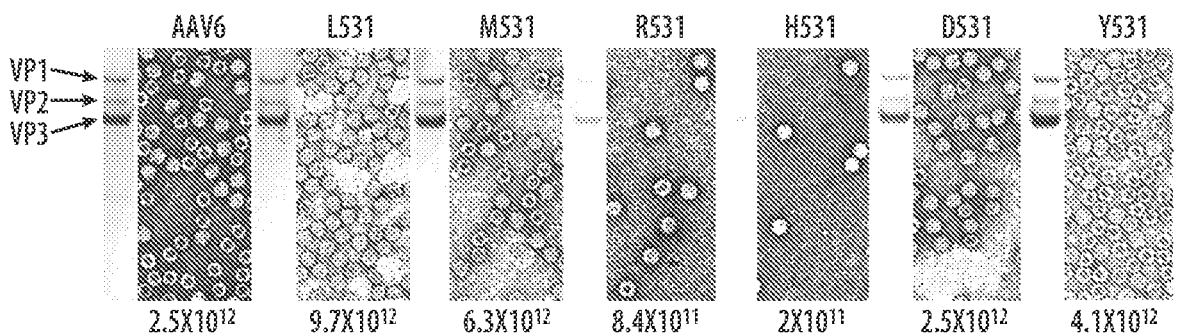
Figure 5B:
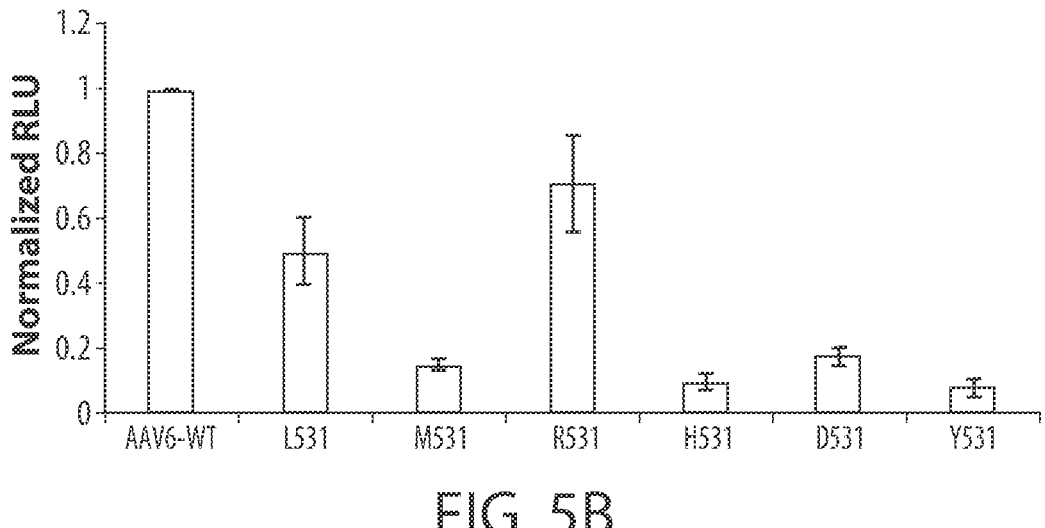

FIGS. 5A-5B show data confirming proper production and purification of wild-type and variant AAV1 and AAV6 particles. FIG. 5A shows negative stained EM of wild-type and variant AAV6 particles. FIG. 5B shows transduction of HEK293 cells with wild-type and variant AAV6 particles.

Figure 6A:
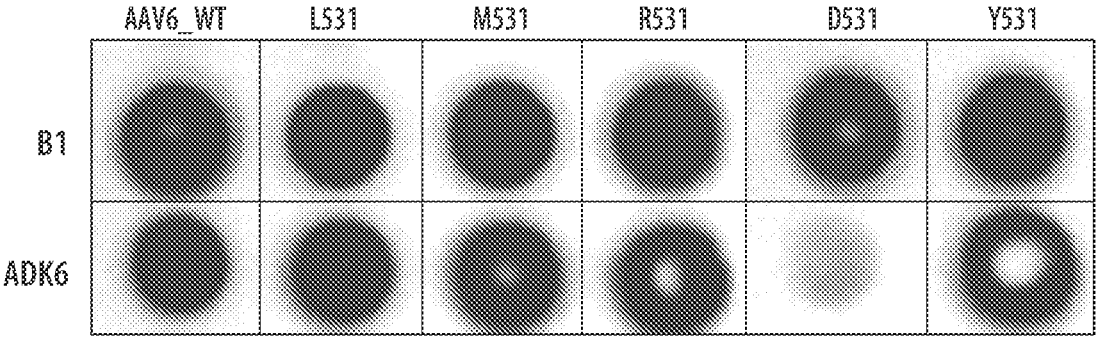
Figure 6B:
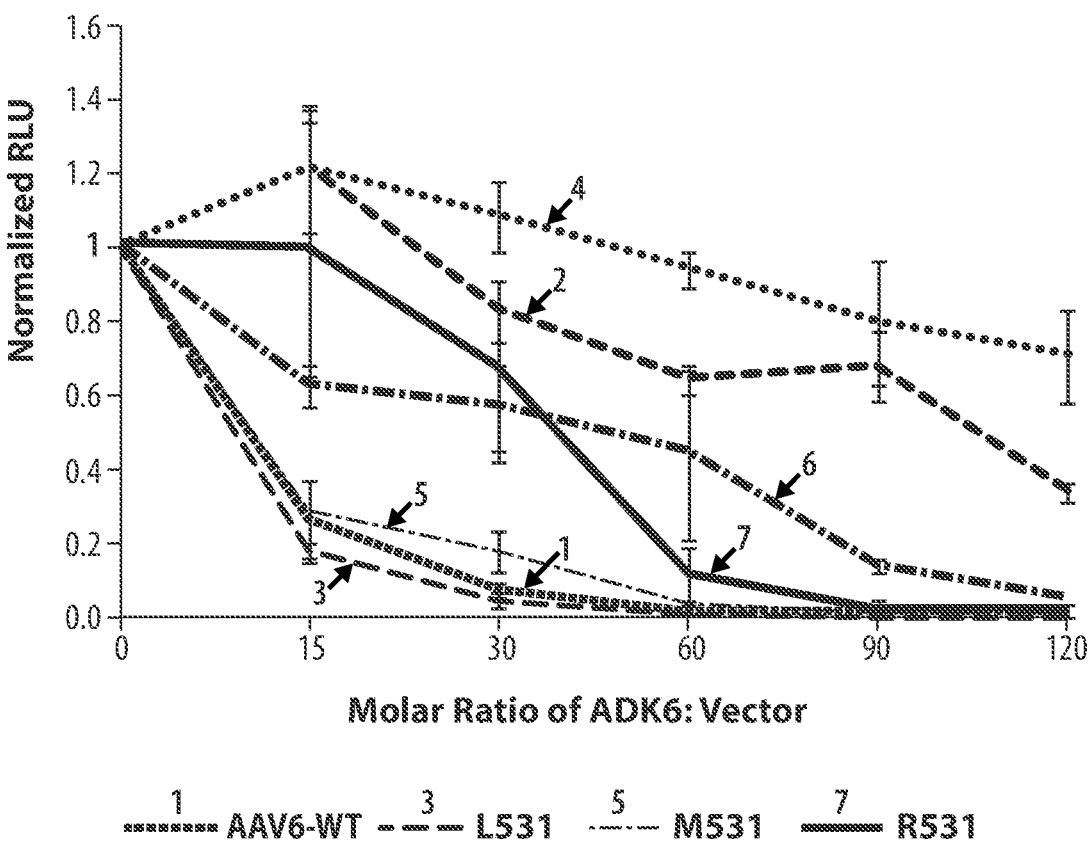

FIGS. 6A-6B show data from ADK6 binding and neutralization assays. FIG. 6A shows an immunoblot of denatured wild-type and variant AAV6 particles detected by B1 (which recognizes a linear epitope of the C-terminus of the VP1/2/3 common region) (top) and by ADK6 (which recognizes native capsids). ADK6 interacts specifically with AAV6, and this interaction is lost in mutant or variant AAV6. FIG. 3B shows data from neutralization assays for wild-type and variants of AAV6 in the presence of ADK6.

DETAILED DESCRIPTION

Adeno-associated viruses (AAVs), small ssDNA viruses with a diameter of ~260 Å, belong to the Dependoparvovirus genus of the Parvoviridae (Agbandje-McKenna and Chapman, 2006; Chapman and Agbandje-McKenna, 2006). The AAV capsid is assembled with a T=1 icosahedral architecture from 60 copies (in total) of three overlapping capsid viral proteins (VPs), VP1, VP2, and VP3, coded from the cap open reading frame by use of alternative transcripts and start sites. The VP sequences are stochastically incorporated into the T=1 capsid in a ratio of 1:1:10 for VP1:VP2:VP3.

AAVs exhibit several features which make them attractive as gene delivery vectors: they are non-pathogenic, can package non-genomic ssDNA and scDNA sequences, can infect dividing and non-dividing cells, and exhibit long-term gene expression. Currently, AAVs represent ~10% of gene therapy clinical trials worldwide (ClinicalTrials.gov), and are being developed for the treatment of several different monogenic diseases, including cystic fibrosis, hemophilia, and muscular dystrophy (Mendell et al., 2009; Nathwani et al., 2011; Wagner et al., 1999).

Although the AAV vector system shows significant promise for gene delivery, one of the limitations is the pre-existing B-cell immunity against different AAV serotypes observed in the general population (Hurlbut et al., 2010; Li et al., 2012; Manno et al., 2006; Zadori et al., 2001). Epidemiological studies report a prevalence of 40-70% seropositivity for AAV, depending on the particular serotype, in people (Boutin et al., 2010). This antibody response has the ability to neutralize AAV vectors, which results in reduced transduction efficiency in target cells or tissue. Furthermore, eligibility for inclusion of a subject in clinical trials requires that the subject be naïve for anti-AAV antibodies (Nathwani et al., 2011).

To that end, the inventors of the present disclosure used a rational design approach to identify amino acid residue K531 of AAV6 capsid protein as a determinant for interacting with and being neutralized by antibody ADK6, which is specific for AAV6 (compared to AAV1).

Variant AAV6 Particles

An AAV "particle" may also be referred to herein as a "vector," or "capsid." Using the knowledge that K531 of VP proteins of AAV6 is a determinant amino acid for interaction between AAV6 capsid and neutralizing antibodies, the inventors of the present disclosure have developed variant rAAV6 capsids with substitutions at amino acid K531 of the capsid proteins (VP1, VP2, and VP3). In some embodiments, a variant rAAV6 capsid as disclosed herein has an acidic or negatively charged amino acid (e.g., aspartic acid, or glutamic acid) at residue 531. In some embodiments, a variant rAAV6 particle as disclosed herein has any one of the following amino acids at position 531 of one or more of its capsid proteins (numbering according to VP1): A, R, N, D, C, E, Q, G, H, I, L, M, F, P, S, T, W, Y, or V. In some embodiments, a variant rAAV6 particle as disclosed herein has any one of the following amino acids at position 531 of one or more of its capsid proteins (numbering according to VP1): E, D, H, Y, R, M, or L. In some embodiments, a variant rAAV6 particle as disclosed herein has any one of the following amino acids at position 531 of one or more of its capsid proteins (numbering according to VP1): E, D, H, Y, or R. In some embodiments, a variant AAV6 particle comprises a glutamic acid at position 531 in one or more of VP1, VP2 or VP3. In some embodiments, a variant AAV6 particle comprises a aspartic acid at position 531 in one or more of VP1, VP2 or VP3. In some embodiments, a variant AAV6 particle comprises a histidine at position 531 in one or more of VP1, VP2 or VP3. In some embodiments, a variant AAV6 particle comprises a tyrosine at position 531 in one or more of VP1, VP2 or VP3. In some embodiments, a variant AAV6 particle comprises a arginine at position 531 in one or more of VP1, VP2 or VP3. In some embodiments, a variant AAV6 particle comprises a methionine at position 531 in one or more of VP1, VP2 or VP3. In some embodiments, a variant AAV6 particle comprises a leucine at position 531 in one or more of VP1, VP2 or VP3.

In some embodiments, a variant rAAV6 particle as disclosed herein has a basic or positively charged amino acid (e.g., arginine, or histidine) at residue 531. In some embodiments, a variant rAAV6 particle as disclosed herein has a hydrophobic amino acid (e.g., glycine, alanine, valine, leucine, isoleucine, proline, phenylalanine, methionine, or tryptophan) at residue 531.

In some embodiments, a variant rAAV6 particle as disclosed herein has a substitution at position K531, and one or more amino acid substitutions at another other amino acid positions in a capsid protein (e.g., VP1, VP2, and/or VP3). In some embodiments, a rAAV6 particle as disclosed herein has a substitution at position K531, and one or more substitutions described in the Examples (for example replacing an amino acid found in wild type AAV6 at one or more positions identified in the Examples with an amino acid not present in wild type AAV6 at the one or more positions). In some embodiments, a rAAV6 particle as disclosed herein has a substitution at position K531, and one or more amino acid substitutions at any of the following positions: N447, S472, V473, N500, T502, and W503. In some embodiments, a rAAV6 particle as disclosed herein has a substitution at position K531, and one or more amino acid substitutions at any of the following positions: S264, G266, N269, H272, Q457, S588, and T589. S264, G266, N269, and H272. In some embodiments, a rAAV6 particle as disclosed herein has a substitution at position K531, and an amino acid substitution at Q457. In some embodiments, a rAAV6 particle as disclosed herein has a substitution at position K531, and one or more amino acid substitutions at any of the following positions: S588 and T589. In some embodiments, a rAAV6 particle as disclosed herein has a substitution at position K531, and one or more amino acid substitutions at one or more positions in any of the following ranges: 262-272, 382-386, 445-457, 459, 469-473, 488-489, 494-496, 499-515, 528-534, 571-579, 584-589 and 593-595. One or more amino acid substitutions at any positon on a capsid protein other than K531 can be basic or positively charged amino acid (e.g., arginine, or histidine), negatively charged (e.g., aspartic acid, glutamic acid), neutral (e.g., asparagine, cysteine, glutamine, glycine, isoleucine, leucine, methionine, phenylanlanine, proline, serine, threonine, tryptophan, tyrosine, or valine), or hydrophobic amino acid (e.g., glycine, alanine, valine, leucine, isoleucine, proline, phenylalanine, methionine, or tryptophan), aliphatic (e.g., alanine, glycine, isoleucine, leucine, or valine), nonpolar (e.g., alanine, cysteine, glycine, isoleucine, leucine, methionine, phenylalanine, proline, tryptophan, or valine) or polar (e.g., arginine, aspartic acid, asparagine, glutamic acid, glutamine, histidine, lysine, serine, threonine, or tyrosine).

In some embodiments, a variant rAAV6 particle as disclosed herein is able to evade neutralization by antibodies that recognize AAV6 particles, compared to their wild-type counterparts. A wild-type counterpart is an AAV6 particle that does not have a substitution at amino acid 531 of capsid protein VP1. A wild-type counterpart of a variant rAAV6 particle as disclosed herein has all the amino acids of capsid proteins of the variant rAAV6 particle, except that it has a different amino acid at position 531 of one or more capsid proteins.

In some embodiments, all three capsid proteins, VP1, VP2 and VP3 have a substitution at position 531 (according to VP1 numbering). In some embodiments, a variant rAAV6 particle is engineered so that only one VP1, VP3, or VP1 and VP3 capsid proteins are expressed. There are 736 amino acids in VP1 of AAV6. VP2 of AAV6 is made up of amino acids 138-736 of AAV6 VP1. VP3 of AAV6 is made up of amino acids 203-736 of AAV6 VP1. An example of the amino acids sequence of wild-type AAV6 capsid protein VP1 is SEQ ID NO: 1.

It is to be understood that amino acid substitutions in one or more capsid proteins as described herein to increase the ability of a rAAV6 particle to evade neutralizing antibodies can be applicable to rAAV particles of other serotypes (e.g., AAV1, AAV2, AAV3, AAV4, AAV5, AAV7, AAV8, AAV9, AAV10, AAV11, AAV12, or AAV13).

Example of AAV6 VP1 Capsid Protein Sequence

```
                                        (SEQ ID NO: 1)
  1 MAADGYLPDW LEDNLSEGIR EWWDLKPGAP KPKANQQKQD
    DGRGLVLPGY

51 KYLGPFNGLD KGEPVNAADA AALEHDKAYD QQLKAGDNPY
    LRYNHADAEF

101 QERLQEDTSF GGNLGRAVFQ AKKRVLEPFG LVEEGAKTAP
    GKKRPVEQSP

151 QEPDSSSGIG KTGQQPAKKR LNFGQTGDSE SVPDPQPLGE
    PPATPAAVGP

201 TTMASGGGAP MADNNEGADG VGNASGNWHC DSTWLGDRVI
    TTSTRTWALP

251 TYNNHLYKQI SSASTGASND NHYFGYSTPW GYFDFNRFHC
    HFSPRDWQRL
```

-continued

```
301 INNNWGFRPK RLNFKLFNIQ VKEVTTNDGV TTIANNLTST
    VQVFSDSEYQ

351 LPYVLGSAHQ GCLPPFPADV FMIPQYGYLT LNNGSQAVGR
    SSFYCLEYFP

401 SQMLRTGNNF TFSYTFEDVP FHSSYAHSQS LDRLMNPLID
    QYLYYLNRTQ

451 NQSGSAQNKD LLFSRGSPAG MSVQPKNWLP GPCYRQQRVS
    KTKTDNNNSN

501 FTWTGASKYN LNGRESIINP GTAMASHKDD KDKFFPMSGV
    MIFGKESAGA

551 SNTALDNVMI TDEEEIKATN PVATERFGTV AVNLQSSSTD
    PATGDVHVMG

601 ALPGMVWQDR DVYLQGPIWA KIPHTDGHFH PSPLMGGFGL
    KHPPPQILIK

651 NTPVPANPPA EFSATKFASF ITQYSTGQVS VEIEWELQKE
    NSKRWNPEVQ

701 YTSNYAKSAN VDFTVDNNGL YTEPRPIGTR YLTRPL
```

In some embodiments, a variant rAAV6 particle as disclosed herein preserves its ability to infect and transduce the target/desired cells, compared to a wild-type rAAV6 particle. In some embodiments, rAAV6 particles as disclosed herein show higher transduction efficiency for a given cell, compared to a wild-type rAAV6 particle. The term "transduction" as used herein refers to the entry of an AAV particle into a cell, and optionally expressing a packaged gene, and is equivalent to "infection" of a cell.

In some embodiments, a variant rAAV6 particle is empty, i.e. it does not comprise any genetic material that can be transferred into an infected cell.

In some embodiments, a variant rAAV6 particle as disclosed herein comprises genetic material which is desired to be transferred into a cell. Accordingly, variant rAAV particles may comprise a nucleic acid vector, which may comprise at a minimum: (a) one or more heterologous nucleic acid regions comprising a sequence encoding a protein or polypeptide of interest or an RNA of interest (e.g., a siRNA or microRNA), and (b) one or more regions comprising inverted terminal repeat (ITR) sequences (e.g., wild-type ITR sequences or engineered ITR sequences) flanking the one or more nucleic acid regions (e.g., heterologous nucleic acid regions). Herein, heterologous nucleic acid regions comprising a sequence encoding a protein of interest or RNA of interest are referred to as genes of interest.

In some embodiments, a gene of interest encodes a detectable molecule (e.g., for the purpose to conducting research studies). In some embodiments, a detectable molecule is a fluorescent protein, a bioluminescent protein, or a protein that provides color (e.g., β-galactosidase, β-lactamases, β-glucuronidase, or spheriodenone). In some embodiments, a detectable molecule is a fluorescent, bioluminescent, enzymatic protein, or functional peptide or functional polypeptide thereof. In some embodiments, a gene of interest encodes a therapeutic protein or therapeutic RNA. In some embodiments, a therapeutic gene encodes an antibody, a peptibody, a growth factor, a clotting factor, a hormone, a membrane protein, a cytokine, a chemokine, an activating or inhibitory peptide acting on cell surface receptors or ion channels, a cell-permeant peptide targeting intracellular processes, a thrombolytic, an enzyme, a bone morphogenetic proteins, a nuclease or other protein used for gene editing, an Fc-fusion protein, an anticoagulant, a nuclease, guide RNA, or other nucleic acid or protein for gene editing.

In some embodiments, the nucleic acid vector that is comprised in an rAAV particle is between 4 kb and 5 kb in size (e.g., 4.2 to 4.7 kb in size). In some embodiments, the nucleic acid vector is circular. In some embodiments, the nucleic acid vector is single-stranded. In some embodiments, the nucleic acid vector is double-stranded. In some embodiments, a double-stranded nucleic acid vector may be, for example, a self-complimentary vector that contains a region of the nucleic acid vector that is complementary to another region of the nucleic acid vector, initiating the formation of the double-strandedness of the nucleic acid vector.

In some embodiments, a variant rAAV6 particle may comprise amino acids of a serotype other than serotype 6 in its capsid, in positions other than 531 (e.g., a chimeric AAV particle). In some embodiments, the serotype of the capsid protein is different from the serotype of the ITRs and/or the Rep gene. In some embodiments, the serotype of the capsid protein of a particle is the same as the serotype of the ITRs. In some embodiments, the serotype of capsid protein of a particle is the same as the serotype of the Rep gene.

Recombinant AAV Particle Compositions

Provided herein are compositions comprising any one of the variant rAAV6 particles described herein. In some embodiments, any one of the compositions provided herein comprises a pharmaceutically acceptable carrier. The term "carrier" refers to a diluent, adjuvant, excipient, or vehicle with which the rAAV particle is administered to a subject. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers. Non-limiting examples of pharmaceutically acceptable carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, polyacrylic acids, lubricating agents (such as talc, magnesium stearate, and mineral oil), wetting agents, emulsifying agents, suspending agents, preserving agents (such as methyl-, ethyl-, and propyl-hydroxy-benzoates), and pH adjusting agents (such as inorganic and organic acids and bases). Other examples of carriers include phosphate buffered saline, HEPES-buffered saline, and water for injection, any of which may be optionally combined with one or more of calcium chloride dihydrate, disodium phosphate anhydrous, magnesium chloride hexahydrate, potassium chloride, potassium dihydrogen phosphate, sodium chloride, or sucrose. Other examples of carriers that might be used include saline (e.g., sterilized, pyrogen-free saline), saline buffers (e.g., citrate buffer, phosphate buffer, acetate buffer, and bicarbonate buffer), amino acids, urea, alcohols, ascorbic acid, phospholipids, proteins (for example, serum albumin), EDTA, sodium chloride, liposomes, mannitol, sorbitol, and glycerol. USP grade carriers and excipients are particularly useful for delivery of rAAV particles to human subjects.

Typically, such compositions may contain at least about 0.1% of the therapeutic agent (e.g., rAAV6 particle) or more, although the percentage of the active ingredient(s) may, of course, be varied and may conveniently be between about 1 or 2% and about 70% or 80% or more of the weight or volume of the total formulation. Naturally, the amount of therapeutic agent(s) (e.g., rAAV6 particle) in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be designed.

In some embodiments, the concentration of rAAV particles administered to a subject may be on the order ranging from $10^6$ to $10^{14}$ particles/ml or $10^3$ to $10^{15}$ particles/ml, or any values therebetween for either range, such as for example, about $10^6$, $10^7$, $10^8$, $10^9$, $10^{10}$, $10^{11}$, $10^{12}$, $10^{13}$, or $10^{14}$ particles/ml. In some embodiments, rAAV particles of a higher concentration than $10^{13}$ particles/ml are administered. In some embodiments, the concentration of rAAV particles administered to a subject may be on the order ranging from $10^6$ to $10^{14}$ vector genomes (vgs)/ml or $10^3$ to $10^{15}$ vgs/ml, or any values therebetween for either range (e.g., $10^6$, $10^7$, $10^8$, $10^9$, $10^{10}$, $10^{11}$, $10^{12}$, $10^{13}$, or $10^{14}$ vgs/ml). In some embodiments, rAAV particles of higher concentration than $10^{13}$ vgs/ml are administered. The rAAV particles can be administered as a single dose, or divided into two or more administrations as may be required to achieve therapy of the particular disease or disorder being treated. In some embodiments, 0.0001 ml to 10 mls are delivered to a subject. In some embodiments, the number of rAAV particles administered to a subject may be on the order ranging from $10^6$-$10^{14}$ vg/kg, or any values therebetween (e.g., $10^6$, $10^7$, $10^8$, $10^9$, $10^{10}$, $10^{11}$, $10^{12}$, $10^{13}$, or $10^{14}$ vgs/mg). In some embodiments, the dose of rAAV particles administered to a subject may be on the order ranging from $10^{12}$-$10^{14}$ vgs/kg. In some embodiments, the volume of rAAV6 composition delivered to a subject (e.g., via one or more routes of administration as described herein) is 0.0001 mL to 10 mLs.

Neutralizing Antibodies and Methods of Measuring Evasion of Neutralizing Antibodies An antibody that is capable of binding to AAV particle and reduces its ability to infect cells is a "neutralizing antibody." In some embodiments, the interaction between neutralizing antibodies and an administered rAAV6 particle results in an immune response.

To measure the ability of a variant or wild-type rAAV6 particle to evade neutralizing antibodies, transduction of cells can be carried out in the presence of neutralizing antibodies. In some embodiments, AAV6 particles are pre-incubated with neutralizing antibodies before allowing them to transduce or infect cells. In some embodiments, a purified antibody known to neutralize AAV particles is used to test the ability of the particles to evade them. Non-limiting examples of neutralizing antibodies to AAV6 are 4E4, 5H7, ADK1, and ADK6 antibody. The Example below describes a method of purifying such antibodies, and also provides one way of measuring neutralization of AAV particles by antibodies. In some embodiments, purified immunoglobulins from a subject or animal model is used as a source of neutralizing antibodies. In some embodiments, the blood or serum of a subject is used as a source of neutralizing antibodies. In some embodiments, neutralization of an rAAV particle is tested at different ratios of particle:neutralizing antibody/ies.

Transduction of a cell by an AAV particle can be tested in a number of different ways. For example, transduction can be measured by measuring the amount of gene that is transferred into a cell (e.g., using methods such as qPCR, and protein assays for protein that is translated from the transferred gene). In some embodiments, transduction can be measured by measuring the amount of virus that is replicated.

Method of Delivering a Gene of Interest to a Subject

As described above, any one of the variant rAAV6 particles disclosed herein has the ability to evade antigenic responses by reducing the interaction with neutralizing antibodies, compared to wild-type counterpart. These variant rAAV particles can be used to deliver one or more genes of interest to a subject who has antibodies capable of neutralizing a rAAV6 particle. Accordingly, provided herein is a method of administering to a subject that is seropositive for AAV6 any one of the variant rAAV6 particles disclosed herein.

A subject is "seropositive for AAV6" if the immune response to an administered rAAV6 particle is statistically higher than the response in a control subject. In some embodiments, a subject is "seropositive for AAV6" if the level of anti-AAV6 antibodies detected in the subject (e.g., in the subject's serum) is statistically higher than the level of anti-AAV6 antibodies detected in a control subject. A control subject may be a subject that has not previously been exposed to AAV particles (e.g., rAAV6 particles). A subject may be "seropositive for AAV6" if exposure to AAV6 particles results in an immune response. In some embodiments, a subject that is seropositive for AAV6 has preexisting anti-AAV6 antibodies and/or T-cells directed against AAV6 epitopes. In some embodiments, a subject may have neutralizing antibodies that recognize AAV6 (i.e., "AAV6 antibodies" or "anti-AAV antibodies") because of a previous exposure to AAVs. The AAVs to which a subject has been previously exposed may be of a natural source (i.e. naturally occurring AAV particles). In some embodiments, AAV particles to which a subject has been previously exposed may be recombinant (i.e. made by man), e.g., for treatment by a therapeutic gene.

An administration of a composition of rAAV particles (e.g., comprising a therapeutic gene) may cause a subject to become seropositive for AAV6. In such instances, it may not be possible to administer rAAV6 particles to the subject, or administering a subsequent rAAV6 particle results in undesired immune response. For such instances, provided herein is a method comprising administering to a subject a subsequent rAAV6 particle, wherein the subsequent rAAV6 particle comprises a capsid protein comprising a substituted amino acid at position 531. In some embodiments, a method comprises administering to a subject a subsequent rAAV6 particle, wherein the subsequent rAAV6 particle is any one of the variant rAAV6 particles disclosed herein. In some embodiments, a subsequent rAAV6 particle is administered within 12 months (e.g., within 12, 11, 10, 9, 8, 7, 6, 5, 4, 3, 2, or 1 month) of the previously received or administered rAAV particle. In some embodiments, a subsequent rAAV6 particle is administered within 1 month (e.g., within 31 days, 30 days, 25 days, 20 days, 21 days, 14 days, 7 days, 5 days, 3 days, 2 days, 1 day, 18 hours, 12 hours, 6 hours, 4 hours, 2 hours, or within 1 hour) of the previously received or administered rAAV particle. In some embodiments, a subsequent rAAV6 particle is administered more than 12 months after (e.g., 1 year, 18 months, 2 years, 3 years, 5 years, 10 years, 20 years, or 50 years after) the previously received or administered rAAV particle.

In some embodiments, a subject has been previously administered a rAAV particle (e.g., rAAV6, or chimeric rAAV particle with amino acids of serotype 6 and one or more capsid protein). In some embodiments, AAV particles to which a subject has been previously exposed are of serotype 1, 2, 3, 4, 5, 6, 7, 8, 9, 10, 11, 12, or 13. In some embodiments, AAV particles to which a subject has been previously exposed is of serotype 6.

In some embodiments, a variant rAAV6 particle that is administered to a subject using any one of the methods provided herein comprises a gene of interest.

Measuring Seropositivity

In some embodiments, a method of administering to a subject that is seropositive for AAV6 a variant rAAV6 particle comprising a capsid protein comprising a substituted amino acid at position 531, further comprises determining whether the subject is seropositive for AAV6.

Methods of determining whether a subject is seropositive for a particular serotype of AAV are known in the art. See e.g., Ferreira et al. (Frontiers in Immunology, 2014, 5(82): 1). In some embodiments, determining whether a subject is seropositive for AAV6 comprises determining whether a subject has anti-AAV6 antibodies and/or T-cells directed against AAV6 epitopes. Presence of anti-AAV6 antibodies in a subject's blood or serum can be detected by incubating a sample of the subject's blood or serum with one or more AAV6 capsid antigens, and thereafter measuring the amount of anti-AAV6 antibodies bound to the one or more AAV6 capsid antigens. Non-limiting examples of capsid antigens include digests of AAV capsids, or a combination of purified capsid peptides, polypeptides, and/or proteins. In some embodiments, only one capsid peptide, polypeptide, or protein is used as an AAV6 antigen. In some embodiments, a protein, peptide, or polypeptide that is used as an antigen has a sequence that is comprised in AAV6 VP1, VP2 or VP3 capsid protein. In some embodiments, a protein, peptide, or polypeptide that is used as an antigen has a sequence that is part of SEQ ID NO:1.

In some embodiments, presence of anti-AAV6 antibodies in a subject's blood or serum can be detected by incubating a sample of the subject's blood or serum with whole capsids.

The amount of antibody bound to capsid antigens or whole capsids can be determined using any number of biochemical and biophysical techniques. See e.g., Neri et al (Trends in Biotechnology, 1996, 14(12): 465), which discusses biophysical methods to determine antibody-antigen affinities, Goldberg et al. (Current Opinion in Immunology, 1993, 5(2): 278), which discusses methods for measuring antibody-antigen affinity based on ELISA and RIA), Quintero-Ronderos et al. (Autoimmunity: From Bench to Bedside, Chapter 48, Analysis of proteins and antibodies, 2013), and Rapti et al. (Mol Ther. 2012 January; 20(1): 73-83), each of which is incorporated herein by reference in its entirety. Non-limiting examples of biochemical approaches to measure interaction between antibodies and antigens and/or capsids include co-immunoprecipitation, bimolecular fluorescence complementation, affinity electrophoresis, ELISA and its various forms (e.g., ELISPOT). Non-limiting examples of biophysical approaches to measure interaction between antibodies and antigens and/or capsids include bio-layer interferometry, dual polarization interferometry, static light scattering, dynamic light scattering, surface plasmon resonance, fluorescence polarization/anisotropy, fluorescence correlation spectroscopy, fluorescence resonance energy transfer, and isothermal titration calorimetry. In some embodiments of detecting anti-AAV6 antibodies, the antigen or capsid is immobilized on a solid support for separating bound antibodies from unbound antibodies. In some embodiments, the solid support are beads.

In some embodiments, determining whether a subject is seropositive for AAV6 comprises determining whether a subject has T-cells directed against AAV6 epitopes. Ferreira et al. (Frontiers in Immunology, 2014, 5(82): 1) describes an assay for AAV1-specific T lymphocytes that can be adapted for AAV6. In some embodiments, a method of determining whether a subject has T-cells directed against AAV6 epitopes comprises incubating peripheral blood mononuclear cells (PBMCs) obtained from the subject with AAV6 capsid antigens. In some embodiments, the PBMCs are purified. In some embodiments, the PBMCs are in blood when assayed. In some embodiments, PBMCs that are assayed are those that secrete interferon gamma. In some embodiments, PBMCs that are obtained from a subject are incubated with AAV6 capsid antigens or whole capsids. As described above, AAV6 capsid antigens can be a digest of AAV capsids, or a combination of purified capsid peptides, polypeptides, and/or and proteins. In some embodiments, only one capsid peptide, polypeptide, or protein is used as an AAV6 antigen. In some embodiments, a protein, peptide, or polypeptide that is used as an antigen has a sequence that is comprised in AAV6 VP1, VP2 or VP3 capsid protein. In some embodiments, a protein, peptide, or polypeptide that is used as an antigen has a sequence that is comprised by SEQ ID NO:1.

Aspects of the disclosure relate to methods for use with a subject, such as human or non-human primate subjects. Non-limiting examples of non-human primate subjects include macaques (e.g., cynomolgus or rhesus macaques), marmosets, tamarins, spider monkeys, owl monkeys, vervet monkeys, squirrel monkeys, baboons, gorillas, chimpanzees, and orangutans. In some embodiments, the subject is a human subject. Other exemplary subjects include domesticated animals such as dogs and cats; livestock such as horses, cattle, pigs, sheep, goats, and chickens; and other animals such as mice, rats, guinea pigs, and hamsters. In some embodiments, a subject is human.

In some embodiments, "administering" or "administration" means providing a material to a subject in a manner that is pharmacologically useful.

In certain circumstances it will be desirable to deliver the rAAV particles in suitably formulated pharmaceutical compositions that are disclosed herein either subcutaneously, intraocularly, intravitreally, subretinally, parenterally, intravenously (IV), intracerebro-ventricularly, intramuscularly, intrathecally (IT), intracisternally, orally, intraperitoneally, by oral or nasal inhalation, or by direct injection to one or more cells, tissues, or organs by direct injection. In some embodiments, the administration is a route suitable for systemic delivery, such as by intravenous injection. In some embodiments, "administering" or "administration" means providing a material to a subject in a manner that is pharmacologically useful.

In some embodiments, any one of the methods of administering to a subject a variant rAAV6 particle as disclosed herein is done to treat a disease, disorder or condition in a subject. To "treat" a disease as the term is used herein, means to reduce the frequency or severity of at least one sign or symptom of a disease or disorder experienced by a subject. The compositions described above or elsewhere herein are typically administered to a subject in an effective amount, that is, an amount capable of producing a desirable result. The desirable result will depend upon the active agent being administered. For example, an effective amount of rAAV particles may be an amount of the particles that are capable of transferring an expression construct to a host organ, tissue, or cell. A therapeutically acceptable amount may be an amount that is capable of treating a disease, e.g., cystic fibrosis, or muscular dystrophy. As is well known in the medical and veterinary arts, dosage for any one subject depends on many factors, including the subject's size, body surface area, age, the particular composition to be administered, the active ingredient(s) in the composition, time and route of administration, general health, and other drugs being administered concurrently.

Any one of the methods of administering to a subject a variant rAAV6 particle as disclosed herein may be performed to treat a lung disease, disorder, or condition (e.g., cystic fibrosis, lung cancer, asthma, chronic obstructive pulmonary disease, chronic bronchitis, emphysema, bronchitis, pneumonia, tuberculosis, pulmonary edema, acute respiratory distress syndrome, sarcoidosis, idiopathic pulmonary fibrosis, or mesothelioma). In some embodiments, any one of the methods disclosed herein is performed to treat a muscle disease (e.g., arthritis, muscular dystrophy, osteoporosis, neurogenic atrophy, congenital myopathy, inflammatory myopathy, toxic myopathy, or a disease of the neuromuscular junction).

Provided herein, is also a method of reducing the antigenic response to rAAV6 particles administered to a subject. In some embodiments, the antigenic response to any one of the variant rAAV6 particles disclosed herein decreases by 5-100% (e.g., 5-100, 5-10, 10-30, 20-50, 20-70, 50-100, 5-60, 20-80 or 80-100%) compared to the antigenic response to a wild-type rAAV6 particle in the same or same type of subject (e.g., same species, same age group of the same species, or same sex of the sample species).

Methods of Making Variant rAAV Particles

A rAAV particle or rAAV composition containing such particles as disclosed herein may comprise a viral capsid and a nucleic acid vector, which is encapsidated by the viral capsid. As mentioned above, in some embodiments, the nucleic acid vector comprises (1) one or more heterologous nucleic acid regions comprising a sequence encoding an RNA, protein or polypeptide of interest, (2) one or more nucleic acid regions comprising a sequence that facilitates expression of the heterologous nucleic acid region (e.g., a promoter), and (3) one or more nucleic acid regions comprising a sequence that facilitate integration of the heterologous nucleic acid region (optionally with the one or more nucleic acid regions comprising a sequence that facilitates expression) into the genome of the subject. In some embodiments, viral sequences that facilitate integration comprise Inverted Terminal Repeat (ITR) sequences. In some embodiments, the nucleic acid vector comprises one or more heterologous nucleic acid regions comprising a sequence encoding an RNA, protein or polypeptide of interest operably linked to a control element (e.g., a promoter), wherein the one or more heterologous nucleic acid regions are flanked on each side with an ITR sequence. Such a nucleic acid vector is herein also referred to as AAV-ITR containing one or more genes of interest. The ITR sequences can be derived from any AAV serotype (e.g., serotype 1, 2, 3, 4, 5, 6, 7, 8, 9, 10, 11, 12, or 13) or can be derived from more than one serotype.

ITR sequences and plasmids containing ITR sequences are known in the art and are commercially available (see, e.g., products and services available from Vector Biolabs, Philadelphia, PA; Cellbiolabs, San Diego, CA; Agilent Technologies, Santa Clara, Ca; and Addgene, Cambridge, MA; and Gene delivery to skeletal muscle results in sustained expression and systemic delivery of a therapeutic protein. Kessler P D, Podsakoff G M, Chen X, McQuiston S A, Colosi P C, Matelis L A, Kurtzman G J, Byrne B J. Proc Natl Acad Sci USA. 1996 Nov. 26; 93(24):14082-7; and Curtis A. Machida. Methods in Molecular Medicine™, Viral Vectors for Gene Therapy Methods and Protocols. 10.1385/1-59259-304-6:201© Humana Press Inc. 2003. Chapter 10. Targeted Integration by Adeno-Associated Virus. Matthew D. Weitzman, Samuel M. Young Jr., Toni Cathomen and Richard Jude Samulski; U.S. Pat. Nos. 5,139,941 and 5,962,313, all of which are incorporated herein by reference).

Genebank reference numbers for sequences of AAV serotypes 1, 2, 3, 3B, 4, 5, 6, 7, 8, 9, 10, 11, 12, and 13 are listed in patent publication WO2012064960, which is incorporated herein by reference in its entirety.

In some embodiments, the nucleic acid vector comprises one or more regions comprising a sequence that facilitates expression of the nucleic acid (e.g., the heterologous nucleic acid), e.g., expression control sequences operatively linked to the nucleic acid. Numerous such sequences are known in the art. Non-limiting examples of expression control sequences include promoters, insulators, silencers, response elements, introns, enhancers, initiation sites, termination signals, and poly(A) tails. Any combination of such control sequences is contemplated herein (e.g., a promoter and an enhancer).

To achieve appropriate expression levels of the protein or polypeptide of interest, any of a number of promoters suitable for use in the selected host cell may be employed. The promoter may be, for example, a constitutive promoter, tissue-specific promoter, inducible promoter, or a synthetic promoter.

For example, constitutive promoters of different strengths can be used. A nucleic acid vector described herein may include one or more constitutive promoters, such as viral promoters or promoters from mammalian genes that are generally active in promoting transcription. Non-limiting examples of constitutive viral promoters include the Herpes Simplex virus (HSV), thymidine kinase (TK), Rous Sarcoma Virus (RSV), Simian Virus 40 (SV40), Mouse Mammary Tumor Virus (MMTV), Ad E1A and cytomegalovirus (CMV) promoters. Non-limiting examples of constitutive mammalian promoters include various housekeeping gene promoters, as exemplified by the β-actin promoter (e.g., chicken β-actin promoter) and human elongation factor-1 α (EF-1α) promoter.

Inducible promoters and/or regulatory elements may also be contemplated for achieving appropriate expression levels of the protein or polypeptide of interest. Non-limiting examples of suitable inducible promoters include those from genes such as cytochrome P450 genes, heat shock protein genes, metallothionein genes, and hormone-inducible genes, such as the estrogen gene promoter. Another example of an inducible promoter is the tetVP16 promoter that is responsive to tetracycline.

Tissue-specific promoters and/or regulatory elements are also contemplated herein. Non-limiting examples of such promoters that may be used include airway epithelial cell-specific promoters, or promoters specific for other cells of the respiratory track.

Synthetic promoters are also contemplated herein. A synthetic promoter may comprise, for example, regions of known promoters, regulatory elements, transcription factor binding sites, enhancer elements, repressor elements, and the like.

The rAAV particle or particle within an rAAV preparation may be of any AAV serotype, including any derivative or pseudotype (e.g., 6, 1/6, 2/6, 3/6, 4/6, 5/6, 7/6, 8/6, 9/6, 10/6, 11/6, 12/6, or 13/6). Pseudotyping refers to using the capsid of one serotype and the genome of another serotype, or the mixing of a capsid and genome from different viral serotypes. These serotypes are denoted using a slash, so that AAV1/6 indicates a virus containing the genome of serotype 1 packaged in the capsid from serotype 6. As used herein, the serotype of an rAAV viral particle refers to the serotype of the capsid proteins of the recombinant virus.

AAV derivatives/pseudotypes, and methods of producing such derivatives/pseudotypes are known in the art (see, e.g., Mol Ther. 2012 April; 20(4):699-708. doi: 10.1038/mt.2011.287. Epub 2012 Jan. 24. The AAV vector toolkit: poised at the clinical crossroads. Asokan A1, Schaffer D V, Samulski R J.). Methods for producing and using pseudotyped rAAV vectors are known in the art (see, e.g., Duan et al., J. Virol., 75:7662-7671, 2001; Halbert et al., J. Virol., 74:1524-1532, 2000; Zolotukhin et al., Methods, 28:158-167, 2002; and Auricchio et al., Hum. Molec. Genet., 10:3075-3081, 2001).

Methods of making or packaging rAAV particles are known in the art and reagents useful for packaging rAAV particles are commercially available (see, e.g., Zolotukhin et al. Production and purification of serotype 1, 2, and 5 recombinant adeno-associated viral vectors. Methods 28 (2002) 158-167; and U.S. Patent Publication Numbers US20070015238 and US20120322861, which are incorporated herein by reference; and plasmids and kits available from ATCC and Cell Biolabs, Inc.). For example, a plasmid comprising a gene of interest may be combined with one or more helper plasmids, e.g., that contain a rep gene (e.g., encoding Rep78, Rep68, Rep52 and Rep40) and a cap gene (encoding VP1, VP2, and VP3, including a modified VP2 region as described herein), and transfected into recombinant cells such that the rAAV particle can be packaged and subsequently purified.

In some embodiments, the packaging is performed in a helper cell or producer cell, such as a mammalian cell or an insect cell. Exemplary mammalian producer cells include, but are not limited to, HEK293 cells, COS cells, HeLa cells, BHK cells, or CHO cells (see, e.g., ATCC® CRL-1573™, ATCC® CRL-1651™, ATCC® CRL-1650™, ATCC® CCL-2, ATCC® CCL-10™, or ATCC® CCL-61™). Exemplary insect producer cells include, but are not limited to Sf9 cells (see, e.g., ATCC® CRL-1711™). Helper cells may comprises rep and/or cap genes that encode the Rep protein and/or Cap proteins for use in a method described herein. In some embodiments, the packaging is performed in vitro. Accordingly, provided herein a helper cells that comprises a nucleic acid encoding any one of the variant rAAV6 capsid proteins disclosed herein, having an amino acid substitution at residue 531. Also provided herein is a nucleic acid encoding any one of the variant rAAV6 capsid proteins disclosed herein, having an amino acid substitution at residue 531.

In some embodiments, a plasmid comprising the gene of interest is combined with one or more helper plasmids, e.g., that contain a rep gene of a first serotype and a cap gene of the same serotype or a different serotype, and transfected into helper cells such that the rAAV particle is packaged.

In some embodiments, the one or more helper plasmids include a first helper plasmid comprising a rep gene and a cap gene, and a second helper plasmid comprising one or more of the following helper genes: E1a gene, E1b gene, E4 gene, E2a gene, and VA gene. For clarity, helper genes are genes that encode helper proteins E1a, E1b, E4, E2a, and VA. In some embodiments, the cap gene is modified such that one or more of the proteins VP1, VP2, and VP3 do not get expressed. In some embodiments, the cap gene is modified such that VP2 does not get expressed. Methods for making such modifications are known in the art (Lux et al. (2005), J Virology, 79: 11776-87)

Helper plasmids, and methods of making such plasmids, are known in the art and commercially available (see, e.g., pDF6, pRep, pDM, pDG, pDP1rs, pDP2rs, pDP3rs, pDP4rs, pDP5rs, pDP6rs, pDG(R484E/R585E), and pDP8.ape plasmids from PlasmidFactory, Bielefeld, Germany; other products and services available from Vector Biolabs, Philadelphia, PA; Cellbiolabs, San Diego, CA; Agilent Technologies, Santa Clara, Ca; and Addgene, Cambridge, MA; pxx6; Grimm et al. (1998), Novel Tools for Production and Purification of Recombinant Adeno associated Virus Vectors, Human Gene Therapy, Vol. 9, 2745-2760; Kern, A. et al. (2003), Identification of a Heparin-Binding Motif on Adeno-Associated Virus Type 2 Capsids, Journal of Virology, Vol. 77, 11072-11081.; Grimm et al. (2003), Helper Virus-Free, Optically Controllable, and Two-Plasmid-Based Production of Adeno-associated Virus Vectors of Serotypes 1 to 6, Molecular Therapy, Vol. 7, 839-850; Kronenberg et al. (2005), A Conformational Change in the Adeno-Associated Virus Type 2 Capsid Leads to the Exposure of Hidden VP1 N Termini, Journal of Virology, Vol. 79, 5296-5303; and Moullier, P. and Snyder, R. O. (2008), International efforts for recombinant adeno-associated viral vector reference standards, Molecular Therapy, Vol. 16, 1185-1188). Plasmids that encode wild-type AAV coding regions for specific serotypes are also know and available. For example pSub201 is a plasmid that comprises the coding regions of the wild-type AAV2 genome (Samulski et al. (1987), J Virology, 6:3096-3101).

An non-limiting example of a rAAV particle production method is described next. One or more helper plasmids are produced or obtained, which comprise rep and cap ORFs for the desired AAV serotype or pseudotype and the adenoviral VA, E2A (DBP), and E4 genes under the transcriptional control of their native promoters. In some embodiments, the one or more helper plasmids comprise rep genes, cap genes, and/or optionally one or more of the adenoviral VA, E2A (DBP), and E4 genes under the transcriptional control of their native promoters. In some embodiments, the one or more helper plasmids comprise cap ORFs (and optionally rep ORFs) for the desired AAV serotype and the adenoviral VA, E2A (DBP), and E4 genes under the transcriptional control of their native promoters. The cap ORF may also comprise one or more modifications to produce a variant capsid protein as described herein. HEK293 cells (available from ATCC®) are transfected via CaPO4-mediated transfection, lipids or polymeric molecules such as Polyethylenimine (PEI) with the helper plasmid(s) and a plasmid containing a nucleic acid vector described herein. The HEK293 cells are then incubated for at least 60 hours to allow for rAAV particle production. Alternatively, the HEK293 cells are transfected via methods described above with AAV-ITR containing one or more genes of interest, a helper plasmid comprising genes encoding Rep and Cap proteins, and co-infected with a helper virus. Helper viruses are viruses that allow the replication of AAV. Examples of helper virus are adenovirus and herpesvirus.

Alternatively, in another example Sf9-based producer stable cell lines are infected with a single recombinant baculovirus containing the nucleic acid vector. As a further alternative, in another example HEK293 or BHK cell lines are infected with a HSV containing the nucleic acid vector and optionally one or more helper HSVs containing rep and cap ORFs as described herein and the adenoviral VA, E2A (DBP), and E4 genes under the transcriptional control of their native promoters. The HEK293, BHK, or Sf9 cells are then incubated for a finite amount of time (e.g., at least 60 hours) to allow for rAAV particle production. The rAAV particles can then be purified using any method known in the art or described herein, e.g., by iodixanol step gradient, CsCl gradient, chromatography, or polyethylene glycol (PEG) precipitation.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: AAV6 K531 Serves a Dual Function in Antibody Recognition

There are currently over 150 genomic sequences of AAV isolated from humans, non-human primates, and other mammalian species. Thirteen serotypes have been described for that represent the range of sequence identity between these viruses (Gao et al., 2004; Gao et al., 2002; Mori et al., 2008; Schmidt et al., 2008). The AAVs are divided onto different groups (group A to F) and clonal isolates (AAV4 and AAV5) based on sequence identities that tends to trend with tissue tropism (Gao et al., 2004). The closely related AAV1 and AAV6, which have ~98% sequence identity, are the representative members of group A. These viruses differ by only 6 out of 736 amino acids in their VP1 sequence, with one of the differences (residue 129) located in VP1u (the unique sequence of VP1, not present in VP2 or VP3), and the remaining five located within the VP3 common region (Wu et al., 2006). Previously, structures determined for AAV1 and AAV6, in which only the VP3 region is ordered, showed two of the differing residues (418 and 642) were located in the interior surface of the capsid while the remaining three residues (531, 584, and 598) were located on the exterior capsid surface (Ng et al., 2010). All five VP3 residues are clustered around the icosahedral 3-fold axis of the capsid associated with receptor attachment and/or transduction determinants for several AAVs (Huang et al., 2016).

Comparative analysis of single amino acid variants in AAV1 and AAV6 at the 6 positions, identified K531 as a determinant of heparan sulfate (HS) receptor binding and liver tropism. Other studies identified K531 as a transduction determinant when combined with AAV1's L129 (Limberis et al., 2009; Wu et al., 2006). Residues involved in sialic acid (SIA) receptor binding by AAV1 and AAV6 are identical and have been mapped to the base of the protrusions surrounding the 3-fold axis (Huang et al., 2016).

Several capsid antibodies generated against AAV1 cross-react with AAV6 and capsid antibody complex structures have shown similar footprints on the AAV1 and AAV6 capsids (Kuck et al., 2007); (Gurda et al., 2012). One of these antibodies, ADK1a, which neutralizes both AAV1 and AAV6, has a footprint overlapping with the SIA binding site suggesting a mechanism of neutralization. However, ADK6, generated against the AAV6 capsid, does not recognize AAV1 (Sonntag et al., 2011). Described below are studies through which the determinant of the selective reactivity of AAV6 to ADK6 was identified by cryo-electron microscopy (cryo-EM) and image reconstruction (cryo-reconstruction). The determinant of the selective recognition by ADK6 was verified using site-directed mutagenesis following by native immunoblots and in vitro neutralization assays.

The experiments described below were carried out with the goal to determine which of the three AAV1/AAV6 capsid surface amino acids (E531K, F584L, A598V; AAV/AAV6 residue types (Ng et al., 2010)) conferred this selective recognition by ADK6. Residue 531 was identified as the determinant of this differential recognition despite the ADK6 footprint covering all three AAV1/6 differing residues and containing residues which overlap with the previously mapped footprints for anti-AAV1 capsid antibodies (Tseng et al., 2015). As mentioned above, K531 is the determinant of HS binding by AAV6, a phenotype that is absent in AAV1, and dictates liver tropism (Wu et al., 2006). The ADK6 footprint also overlapped the previously mapped common SIA binding site residues, N447, S472, V473, N500, T502, and W503, for AAV1 and AAV6. These observations indicate a block of both HS and SIA binding as the mechanism of ADK6 neutralization of AAV6. This study thus provides residue level information that is used to engineer AAV1 and AAV6 vectors with desired tissue tropism and antibody escape properties.

Materials and Methods

Production and Purification of AAV6 Virus-Like Particles

The production and purification of AAV6 virus-like particles (VLPs) using the Baculovirus/SF9 expression system has been previously described (DiMattia et al., 2005; Miller et al., 2006; Ng et al., 2010). Briefly, a baculovirus packaging a gene containing the DNA for expressing the AAV6 VP2 and VP3 was made using the Bac-to-Bac system according to the manufacturer's instructions (Invitrogen) and used to infect SF9 cells. The cell pellet from the infection was resuspended in TNTM buffer (25 mM Tris-HCl, pH 8.0, 100 mM NaCl, 0.2% Triton X-100, 2 mM MgCl2), freeze/thawed 3× with Benzonase (Promega) treatment at 37° C. after the second thaw, and clarified by centrifugation at 10,000 rpm in a JA-20 rotor at 4° C. for 20 min. The supernatant was loaded on a 20% sucrose cushion (w/v of sucrose in TNTM buffer) and the sample centrifuged at 45,000 rpm on a Ti70 rotor at 4° C. for 3 hr. The supernatant was discarded and the pellet was resuspended in TNTM and left stirring overnight at 4° C. The resuspended pellet was loaded onto a 5-40% (w/v) sucrose step gradient and the sample centrifuged at 35,000 rpm in an SW41 rotor for at 4° C. for 3 hr. The VLP containing fraction collected by fractionation, dialyzed into Buffer A (20 mM Tris-HCl, pH 8.5, 15 mM NaCl) and the sample further purified by ion exchange chromatography before use.

A 1 ml anion exchange column (Q, GE Healthcare) was equilibrated with 5 column volumes (CV) of Buffer A, charged with 5 CV of Buffer B (20 mM Tris-HCl, pH 8.5, 500 mM NaCl) and a final wash of 10 CV with Buffer A. The sample was loaded on the column at 0.5 ml/min, the column was washed with 10 CV of Buffer A, and the sample was eluted with a 5 CV gradient from 0-100% Buffer B (Zolotukhin et al., 2002). Five hundred microliter fractions were collected and screened to identify the fractions containing AAV6 VP. These fractions were pooled, buffer exchanged into PBS, concentrated to 1 mg/ml, and analyzed by SDS PAGE and negative stain electron microscopy (EM) to check for purity and capsid integrity, respectively.

Purification of ADK6 IgG Antibodies

The ADK6 immunoglobulin G (IgG) antibody was produced by the University of Florida Hybridoma Core Lab as previously described (Kuck et al., 2007; Tseng et al., 2016). The ADK6 hybridoma supernatant was diluted 1:5 with PBS and loaded onto a 1 ml HiTrap protein G HP column (GE Healthcare), washed with 10 CV of PBS, eluted with 0.5 ml of Glycine-HCl at pH 2.7, and neutralized with 50 μl of neutralization buffer (1 M Tris-HCl pH 10). The purified IgG was buffer exchanged into 20 mM Sodium Phosphate pH 7.0, 10 mM EDTA, and concentrated for papain cleavage.

ADK6 Fragment Antibody (FAb) Generation and Purification

Cysteine HCl was added to the papain digestion buffer (20 mM sodium phosphate pH 7.0, 10 mM EDTA) immediately prior to use. Concentrated IgGs were incubated with immobilized papain (Pierce) at an enzyme:substrate ratio of 1:160 at 37° C. for 16 h. An equal volume of papain stop buffer (10 mM Tris-HCl pH 7.5) was added to stop the cleavage process and the mixture was centrifuged at 1500×g for 2 min to separate the sample from the immobilized papain. The FAbs were separated from the undigested IgG and fragment crystallizable (Fc) fragments on a HiTrap Protein A column (GE Healthcare). The FAbs were collected in the wash and flowthrough fractions, buffer exchanged into PBS, and concentrated for use.

AAV6-ADK6 FAb Complex Formation

AAV6 VLPs at a concentration of 1 mg/ml and ADK6 FAbs at a concentration of 1 mg/ml were mixed at a molar ratio of 1:1 and 2:1 FAb:VP binding site, and the mixture was incubated at 4° C. for 1 h. The complexes were examined by negative stain EM on a Spirit microscope (FEI) to confirm capsid decoration by FAbs prior to vitrification for cryo-EM data collection.

AAV6-ADK6 FAb Complex Cryo-EM Data Collection.

Three microliters of the AAV6-ADK6 FAb complex mixture were loaded onto C-Flat holey carbon grids (CF-2/2-4C-50, Protochips Inc.) that were glow discharged for 1 min prior to use, and vitrified by plunge freezing into liquefied ethane in a Vitrobot Mark IV (FEI). The frozen grids were transferred to liquid nitrogen and then into a FEI Technai TF20 transmission electron microscope operating at 200 kV. Cryo micrographs were collected using a defocus range of 2.5-3.0 μm and total dosage of 20e-/Å2 per image. Thirty-six micrographs were collected with a Gatan Ultra Scan 4000 CCD camera at a step size of 1.82 Å/pixel.

Cryo-EM and Image Reconstruction of the AAV6-ADK6 FAb Complex

The RobEM software package (http://cryoEM.ucsd.edu/programs.shtm) was used to extract decorated AAV6 VLPs (complexed) particles from each micrograph. The defocus level for each micrograph was estimated using the CTFFIND3 application (Mindell and Grigorieff, 2003) incorporated into the AUTO3DEM application (Yan et al., 2007a; Yan et al., 2007b). Preprocessing of the selected particles to remove blemishes, correct linear gradient, normalize, and apodize the images used the "autopp" subroutine within the AUTO3DEM software package and an initial model, at ~25 Å resolution, was generated for searching and initiating the refinement of each particle origin and orientation using the same application (Yan et al., 2007a). Following an initial 10 cycles of search and refinement, the data set was "re-boxed" and "re-centered" using the refined particle center and orientation information, and the images were corrected to compensate for the effect of phase reversal in the contrast transfer function (CTF) followed by additional cycles of refinement also within AUTO3DEM (Yan et al., 2007b). The final resolution was determined by the Fourier shell correlation (FSC) threshold of 0.5 (van Heel and Schatz, 2005). The images of the reconstructed map were illustrated using the Chimera software package (Petersen et al., 2004).

Pseudo-Atomic Model Fitting and Identification of the ADK6 Antibody Footprint

The AAV6 60mer VP3 capsid coordinates were generated by icosahedral matrix multiplication using the Oligomer generator subroutine using the Viperdb online server (http://viperdb.scripps.edu/) (Carrillo-Tripp et al., 2009) from the AAV6 crystal structure (RCSB PDB ID no: 3OAH). The coordinates were fitted into the cryo-EM reconstructed complex density map by rigid body rotations and translations using the Chimera program (Pettersen et al., 2004). This 60mer docked with a correlation coefficient (CC) of 0.94. To enable model building into the FAb density, a difference map, subtracting a scaled density map generated for the docked 60mer model from the AAV6-ADK6 complex map, was generated. A generic FAb structure (PDB ID no: 2FBJ) was fitted into the resulting positive difference density map representing the FAb interacting with the reference AAV6 VP3 monomer (chain A) using the Chimera program (Pettersen et al., 2004). The coordinates for the reference monomer was extracted from the docked 60mer and together with the docked Fab model was used to generate a 60mer using Viperdb (http://viperdb.scripps.edu/) (Carrillo-Tripp et al., 2009). This complex 60mer was then re-docked into the reconstructed complex density map and the CC was similar at 0.93. To determine the interacting residues between the AAV6 capsid and ADK6 FAbs the PDBePISA (http://www.ebi.ac.uk/msd-srv/prot_int/) (Krissinel and Henrick, 2007) and COOT (Emsley et al., 2010) software packages were used. Images for the co-ordinates of the fitted complex were generated using the PyMol program (http://www.pymol.org/) (Schrödinger, 2017).

Recombinant Wild-Type and Variant AAV1 and AAV6 Vector Production and Purification To identify the critical residue determinant for ADK6 recognition by AAV6 (and not AAV1) recombinant wild-type (WT) AAV1 (rAAV1) and AAV6 (rAAV6), and reciprocal single site directed variants, at the equivalent capsid surface amino acid positions 531 and 584, K and F in AAV6 and E and L in AAV1, respectively, located within the ADK6 footprint, and AAV6-V598A were made for testing by native immunoblot and infectivity in the presence of ADK6. As a negative control of a differing non-footprint residue (interior capsid surface) and control for AAV6 capsid assembly in the presence of the amino acid substitution, the reciprocal AAV6-H642N variant was also created for testing. These variants were made as previously described in the pXR1 and pXR6 backgrounds, for AAV1 and AAV6, respectively (Wu et al., 2006).

To produce wild-type and variant rAAV1 and rAAV6 vectors, monolayers of HEK293 cells, at 70% confluency, were triply transfected with 18 μg of wild-type and mutant pXRAAV1 and pXRAAV6 plasmids, 18 μg of pTR-UF3-Luciferase (luciferase gene between AAV2 inverted terminal repeats), and 54 μg of the helper plasmid pXX6, with 190 μl of Polyethyleneimine (1 mg/ml) per 15 cm plate. Ten 15 cm plates were transfected for each vector followed by incubation at 37° C. for 72 h in the presence of 5% CO2. Post transfection, the cells were harvested and centrifuged at 1100×g for 15 min. The supernatant for each vector was precipitated with 10% PEG 8000 (Fisher) and the cell pellets were resuspended in 10 ml TD buffer (1×PBS, 5 mM MgCl2 and 2.5 mM KCl, pH7.4) and freeze/thawed 3× to release virus from the cells. Both the PEG precipitated virus resuspended in TD buffer and the resuspended cell lysate were Benzonase (Novagen) treated at 37° C. for 1 h followed by clarification by centrifugation at 10,000 rpm in a JA-20 rotor at 4° C. for 20 min. The genome containing vectors were separated from the empty capsids by a step Iodixanol gradient (Zolotukhin et al., 2002). In brief, the clarified supernatants were loaded onto a 15-60% step iodixanol gradient. The 40/60% interface or vector containing fractions was collected and diluted with 10×TD buffer. The genome containing vectors were further purified by AVB (Thermo Fisher) affinity column chromatography (Mietzsch et al., 2014). A 1 ml AVB column was equilibrated with 10 ml TD buffer, and the diluted vector containing fractions were loaded at 1 ml/min. The purified vector was eluted with 10 ml or 10 CV elution buffer (0.1M Na Acetate pH=2.5 and 0.75M NaCl at 0.5 ml fractions). The elution fractions were diluted with 50 μl neutralization buffer (1M Tris-HCl pH=10). The purified vectors were buffer exchanged into PBS buffer and quantified by UV spectrometry analysis and qPCR.

Native Immunoblots

To confirm the interaction of AAV6 with ADK6 and the lack of recognition of AAV1 by the antibody, and to further delineate the specific residue(s) important for the capsid antibody binding, the purified rAAV1 and rAAV6 vectors and the single residue variants, rAAV1-E531K (AAV1-K531), rAAV1-F584L (AAV1-L584), rAAV6-K531E (AAV6-E531), rAAV6-L584F (AAV6-F584), and rAAV6-H642N (AAV6-N642) vectors were probed by native immunoblot with ADK6. One hundred ng of purified intact vectors were loaded on a nitrocellulose membrane. The membrane was blocked with 5% milk (w/v) in PBS and 0.05% Tween (1 h), followed by 1 h incubation with ADK6 (0.5 mg/ml) diluted 1:3000. The rAAV-ADK6 complexes were probed with the Horse Radish Peroxidase (HRP) anti-mouse secondary antibody diluted 1:5000. The membrane was finally probed with chemiluminescent and detected on a Kodak film. The film image was documented with a Gel Doc (Biorad). As a positive control 100 ng of rAAV vectors were boiled at 100° C. for 5 min and the sample loaded on a nitrocellulose membrane. The sample was then probed with the B1 antibody that recognizes the C-terminus of the rAAV1 and rAAV6 VP. This C-terminus epitope is only available when the capsid is denatured (Wobus et al., 2000).

Neutralization Assays

To determine if binding of ADK6 to the wild-type and variant rAAV vectors is neutralizing in vitro, purified vectors were used to infect HEK293T cells in the presence of the antibody as previously described (Tseng et al., 2015). Briefly, HEK293T cells were seeded in 96 well plates at 1.25×104 259 cells/well for 24 h to reach 70% confluency. The purified wild-type and mutant vectors (2.5×109 260 vg) were incubated at virus particle:ADK6 IgG molecular ratios of 1:0, 1:15, 1:30, 1:60, 1:90 and 1:120 in PBS in a final volume of 30 μl in unsupplemented DMEM (Gibco) at 37° C. for 1 h. After this incubation period, the media was aspirated from the cells, the complex sample was added to 70 μl of DMEM supplemented with 10% FBS and 1% Antibiotic and antimytotic (ABAM), and the mixture was added to the cells. The cells were incubated at 37° C. for 48 h in the presence of 5% CO2. The cells were harvested, washed with PBS, lysed, and transduction level determined by the Luciferase Assay System (Promega) according to the manufacturer's instruction.

Results

Cryo-Reconstruction of the AAV6-ADK6 Complex.

Figure 1A:
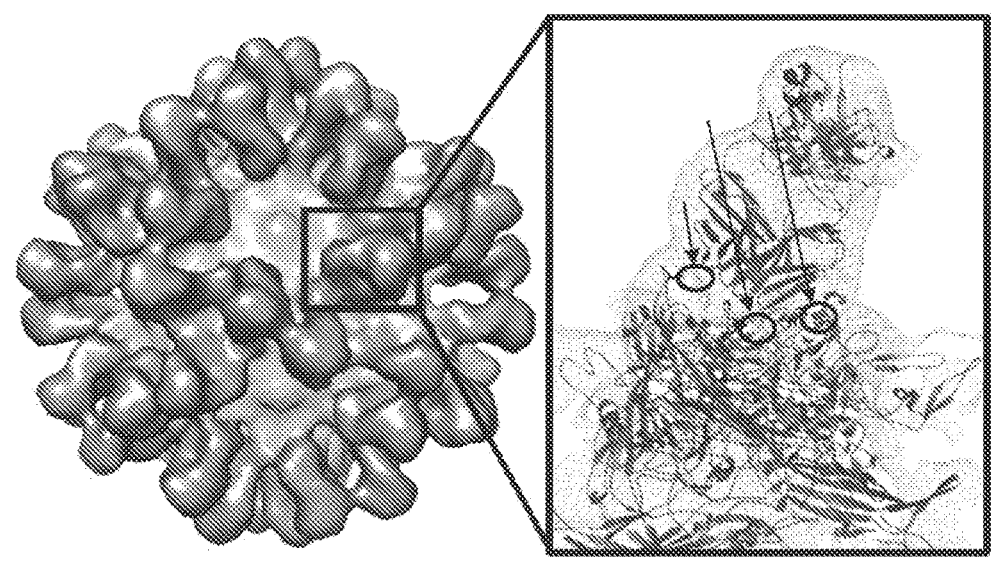
FIGS. 1A-1C show AAV6-ADK6 FAb complex structure.
Figure 1B:
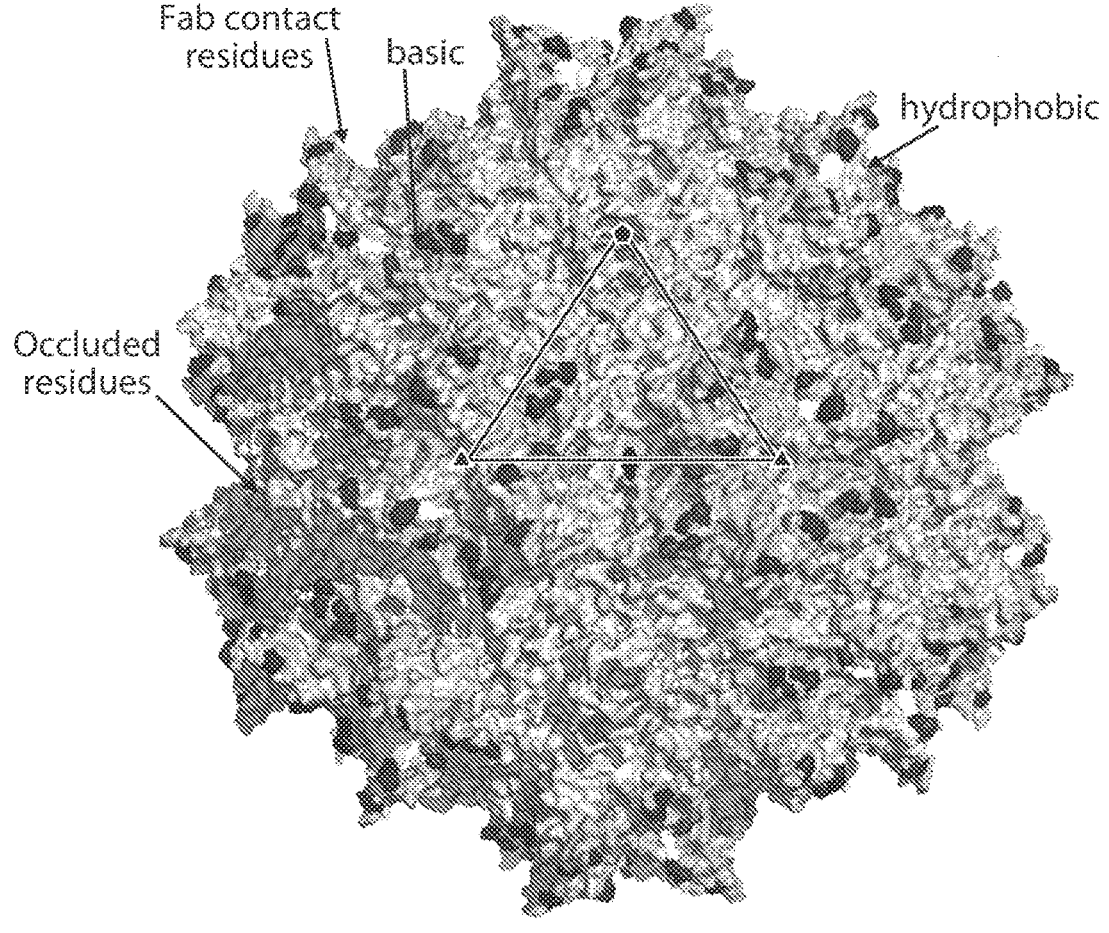
Figure 1C:
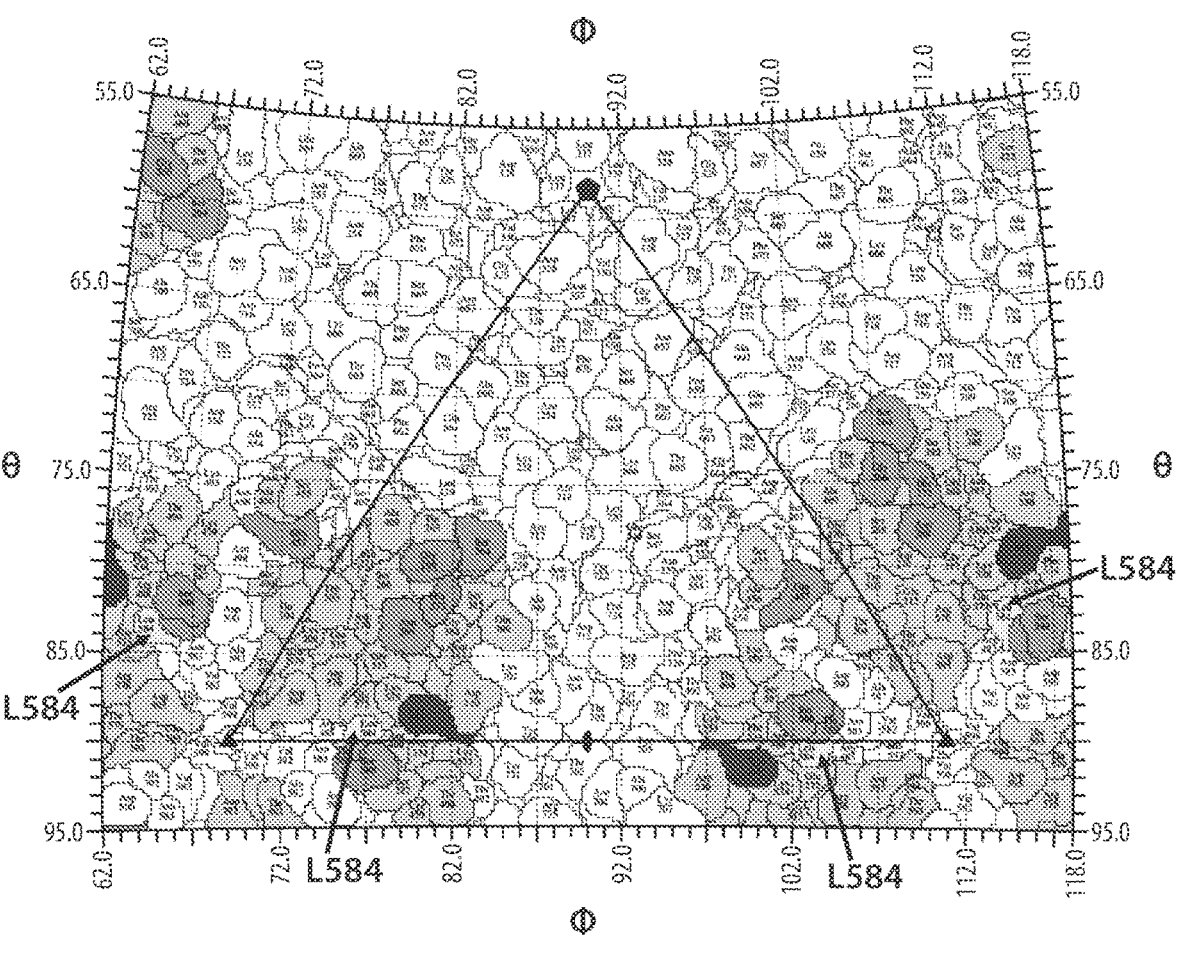

The cryo-EM reconstruction of the AAV6:ADK6 FAb complex, determined to 16 Å resolution, shows ADK6 FAbs bound to the side of the 3-fold protrusion across the 2-fold axis of the AAV6 capsid surface suggesting bivalent binding (FIGS. 1A-1C). Consistent with this observation, a complex with an intact ADK6 IgG (uncleaved) showed a similar structure to the FAb alone with no ordered density for the Fc. The ADK6 binding site on the AAV6 capsid is within a common antigenic site utilized by the other AAVs, the 3-fold protrusions and the 2/5-fold wall (Tseng et al., 2015). These epitopes are regions of high sequence and structural diversity and shown to be important for receptor recognition and transduction by the AAVs. The contact residues between AAV6 and the ADK6 FAb in the pseudo-atomic model fitted into the reconstructed density map, with CC of 0.93, are shown in FIG. 1C.

The AAV6 capsid surface residues which make contact with the docked ADK6 FAb model residues identified by the PDBePISA program are S264, G266, N269, H272, Q457, S588, and T589. Residues S264, G266, N269, and H272 are located on one 3-fold symmetry related monomer, Q457 on a second 3-fold related monomer, and residues S588 and T589 were located on the third 3-fold related monomer. Additionally, the ADK6 Fab footprint occludes other residues surrounding the model contact residues: 262-272, 382-386, 445-457, 459, 469-473, 488-489, 494-496, 499-515, 528-534, 571-579, 584-589 and 593-595. Significantly, two of the residues that differ between AAV1 and AAV6, 531 and 584, are located in the occluded region (FIGS. 1B-1C). Only AAV6, but not AAV1, binds to ADK6 (Sonntag et al., 2011). Thus, the footprint implied that the specificity of the AAV6:ADK6 interaction is dictated by 531, 584 or both.

Reciprocal AAV1 and AAV6 Vectors are Comparable to Wild-Type in Capsid Assembly and Genome Titer FIG. 2A shows residues present in positions 531, 584, 598, and 642 in AAV1 and AAV6. The AAV1 and AAV6 variants purified by AVB column chromatography showed assembled capsids when visualized by negative stain EM (FIG. 2B), and had packaged genome titers in the $10^{10}$-$10^{13}$ vg/ml range, which is comparable to that of wild-type virus (FIG. 2C). The AAV6-N642 variant, with a change on the interior surface of the capsid, also assembled capsids and packaged genome at levels comparable to wild-type. These observations confirmed that the mutations made had no significant effect on capsid assembly and genome packaging.

AAV6 K531 is Responsible for ADK6 Recognition

Figure 3A:
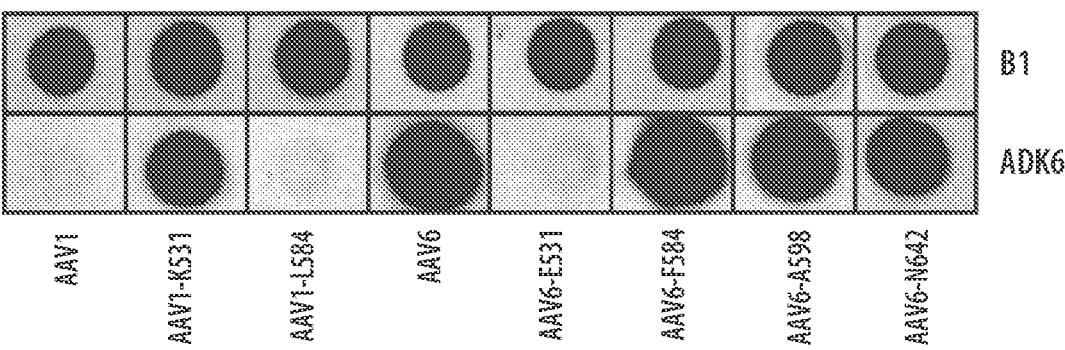
FIGS. 3A-3C show data from ADK6 binding and neutralization assays.
Figure 3B:
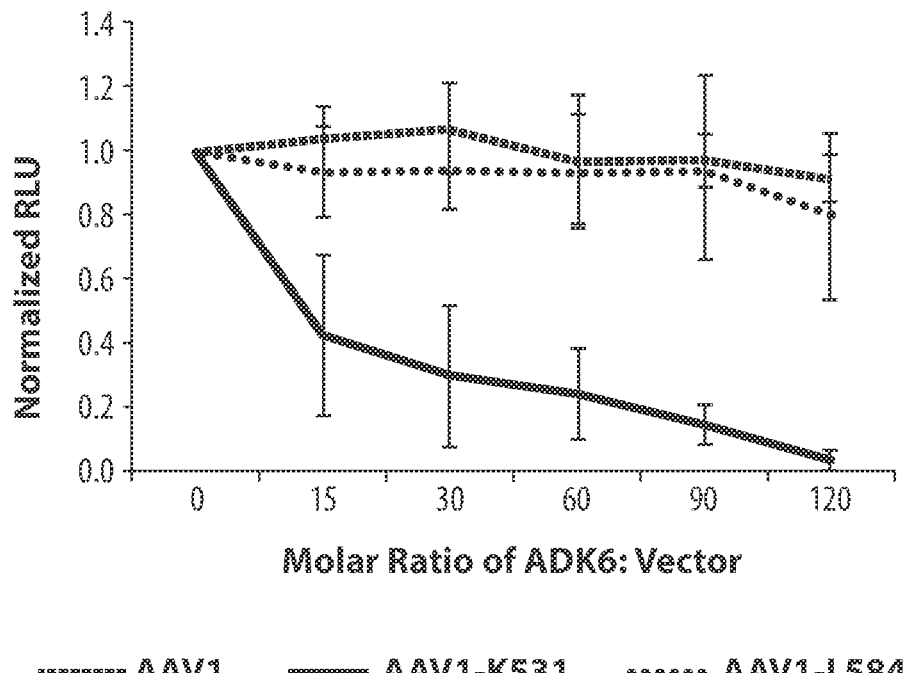
Figure 3C:
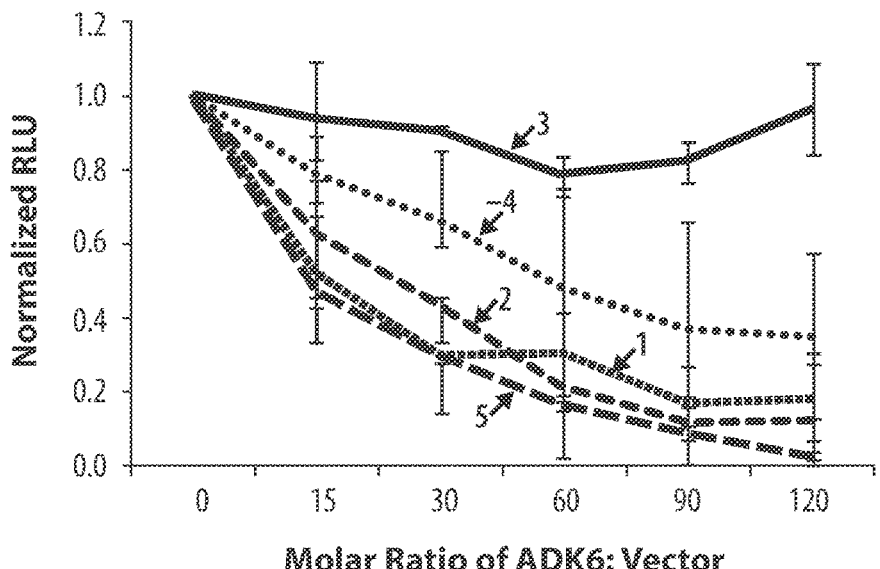

Immunoblots of AAV1 and AAV6 with ADK6 confirmed the recognition of AAV6 by ADK6 and the escape by AAV1 (FIG. 3A). The immunoblots showed that ADK6 recognizes variant AAV1-K531, with an E to K change switching the AAV1 residue type to AAV6, but not AAV1-F584 with an L to F switch at the second occluded position (FIG. 3A). This observation identified AAV6-K531 as being the determinant of ADK6 recognition. Consistent with this conclusion, ADK6 recognizes AAV6-F584 and AAV6-N642 and not AAV6-E531 (FIG. 3A). AAV1 and AAV1-L584 escape from ADK6 while AAV1-K531 is neutralized by ADK6 at a molar ratio of ~15 FAb molecules per capsid (FIG. 3B). This is only 25% binding site occupancy. ADK6 neutralization results in 50% inhibition of transduction for AAV6 and AAV6-F584, also at a molar ratio of ~15 FAb molecules per capsid, AAV6-A598 with ~20 FAb molecules, and AAV6-N642 with ~60 FAb molecules (FIG. 3C). On the other hand, AAV6-E531 escapes antibody recognition at up to a molar ratio of 120 FAb molecules per capsid, a saturation of 2 FAb molecules per VP binding site (FIG. 3C). These observations confirm the role of K531 as the determinant of the specificity of ADK6 for AAV6 and highlights the important contributions of capsid residues that may not make direct contact with FAb residues but are part of the footprint in virus-antibody interactions.

ADK6 Binding is Predicted to Sterically Hinder AAV6 Glycan Binding and has a Footprint that Overlaps Previously Defined Epitopes AAV6 is a dual glycan receptor binding serotype that utilizes both HS and SIA for cellular infection (Huang et al., 2016; Wu et al., 2006). The ADK6 footprint covers a large area of the AAV6 capsid surface including the previously structurally mapped SIA glycan receptor binding site in addition to K531 reported to be responsible for its HS binding (FIGS. 4A and 4B) (Huang et al., 2013; Wu et al., 2006). The ability of ADK6 to block transduction by AAV6 indicates that ADK6 neutralizes AAV6 infection at the entry step, likely by steric hindrance of both glycan interactions. The block of SIA interaction is similar to the mechanism proposed for ADK1a neutralization of AAV1 and AAV6 which shares regions of the ADK6 footprint at the top of the 3-fold region (Huang et al., 2016; Tseng and Agbandje-McKenna, 2014). This mechanism is different to those reported for the A20 neutralization of AAV2 and ADK8 neutralization of AAV8 (Gurda et al., 2012; Huttner et al., 2003; McCraw et al., 2012; Tseng et al., 2015). These antibodies are proposed to neutralize at a post-entry step, with A20 acting in the nucleus and ADK8 blocking nuclear entry and resulting in perinuclear accumulation. While an AAV8 cell surface glycan receptor is unknown, AAV2 binds its HS receptor at the 3-fold axis, a region disparate from the A20 footprint located at the 2/−5-fold wall (McCraw et al., 2012). The ADK6 footprint on AAV6 overlaps that previously mapped for other AAV-antibody interactions, including AAV8-ADK8, AAV1-ADK1a, and regions of AAV1-5H7, AAV6-5H7, and AAV2-A20 on the 3-fold protrusions and the 2/5-fold walls (Gurda et al., 2012; Tseng and Agbandje-McKenna, 2014; Tseng et al., 2015; Tseng et al., 2016). This structure thus adds to the library of antigenic footprint information being accumulated for the AAVs and informs the engineering of a generation of AAV vectors with the ability to evade pre-existing host immune responses during the vector re-administration.

This study, using a combination of structure, site-directed mutagenesis, and cell binding assays, identified a single residue, K531, as conferring antigenic selectivity between the closely related AAV1 and AAV6. Significantly, repeat administration of the approved AAV1 based lipoprotein lipase gene vector treatment will require the use of an antigenic variant with similar transduction properties. The observation that position 531 of AAV1/6 is able to provide immune escape properties is the basis for engineering AAV vectors (or particles) that can evade an antigenic response for use in these patients as well as those that are seropositive for AAV6 or AAV1 for any other reason that being previously administered AAV vectors.

Example 2: Effect of Further Amino Acid Substitutions at Position 531 of AAV6 Capsids to Reduce Neutralization by ADK6 Antibody AAV6 capsids were made with the following substitutions at position 531 of the VP1, VP2 and VP3: D, H, R, Y, M, and L. All AAV6-531 mutants generated assembled capsids from VP1, VP2, and VP3 in the appropriate ratio (FIG. 5A). The capsids also packaged genome ranging from 2.0×1011vg/ml −9.7×1012 vg/ml (FIG. 5A, bottom). All mutants generated transduced HEK293, with the infectivity of R531 being the closest to that of wild-type AAV6 in terms of quantity of luciferase expression (FIG. 5B). With respect to neutralization, D531 showed the greatest escape from ADK6 while H531, Y531, and R531 show increasing levels of escape (FIGS. 6A and 6B). The two hydrophobic residues, L531 and M531 are equally neutralized as wild-type AAV6 (FIGS. 6A and 6B).

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or"

should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

REFERENCES

Agbandje-McKenna, M., Chapman, M. S., 2006. *Structure-function relationships*, in: M. E. Bloom, S. F. C., R. M. Linden, C. R. Parrish, and J. R. Kerr (Ed.), In Parvoviruses. Edward Arnold, 	 Ltd, London, pp. 125-139.

Boutin, S., Monteilhet, V., Veron, P., Leborgne, C., Benveniste, O., Montus, M. F., Masurier, C., 2010. Prevalence of serum IgG and neutralizing factors against adeno-associated virus (AAV) types 1, 2, 5, 6, 8, and 9 in the healthy population: implications for gene therapy using AAV vectors. Hum Gene Ther 21, 704-712.

Buller, R. M., Rose, J. A., 1978. Characterization of adeno-virus-associated virus-induced polypeptides in KB cells. J Virol 25, 331-338.

Buning, H., Braun-Falco, M., Hallek, M., 2004. Progress in the use of adeno-associated viral vectors for gene therapy. Cells Tissues Organs 177, 139-150.

Carrillo-Tripp, M., Shepherd, C. M., Borelli, I. A., Venkataraman, S., Lander, G., Natarajan, P., Johnson, J. E., Brooks, C. L., 3rd, Reddy, V. S., 2009. VIPERdb2: an enhanced and web API enabled relational database for structural virology. Nucleic Acids Res 37, D436-442.

Chapman, M. S., Agbandje-McKenna, M., 2006. *Atomic structure of viral particles*, in: M. E. Bloom, S. F. C., R. M. Linden, C. R. Parrish, and J. R. Kerr (Ed.), In Parvoviruses. Edward Arnold, 	 Ltd, London, pp. 109-123.

DiMattia, M., Govindasamy, L., Levy, H. C., Gurda-Whitaker, B., Kalina, A., Kohlbrenner, E., Chiorini, J. A., McKenna, R., Muzyczka, N., Zolotukhin, S., Agbandje-McKenna, M., 2005. Production, purification, crystallization and preliminary X-ray structural studies of adeno-associated virus serotype 5. Acta Crystallogr Sect F Struct Biol Cryst Commun 61, 917-921.

Emsley, P., Lohkamp, B., Scott, W. G., Cowtan, K., 2010. Features and development of Coot. Acta Crystallogr D Biol Crystallogr 66, 486-501.

Gao, G., Vandenberghe, L. H., Alvira, M. R., Lu, Y., Calcedo, R., Zhou, X., Wilson, J. M., 2004. Clades of Adeno-associated viruses are widely disseminated in human tissues. J Virol 78, 6381-6388.

Gao, G. P., Alvira, M. R., Wang, L., Calcedo, R., Johnston, J., Wilson, J. M., 2002. Novel adeno-associated viruses from rhesus monkeys as vectors for human gene therapy. Proc Natl Acad Sci USA 99, 11854-11859.

Gaudet, D., Methot, J., Kastelein, J., 2012. Gene therapy for lipoprotein lipase deficiency. Curr Opin Lipidol 23, 310-320.

Gurda, B. L., Raupp, C., Popa-Wagner, R., Naumer, M., Olson, N. H., Ng, R., McKenna, R., Baker, T. S., Kleinschmidt, J. A., Agbandje-McKenna, M., 2012. Mapping a neutralizing epitope onto the capsid of adeno-associated virus serotype 8. J Virol 86, 7739-7751.

Huang, L. Y., Patel, A., Ng, R., Miller, E. B., Halder, S., McKenna, R., Asokan, A., Agbandje-McKenna, M., 2016. Characterization of the Adeno-Associated Virus 1 and 6 Sialic Acid Binding Site. J Virol 90, 5219-5230.

Huang, X., Hartley, A. V., Yin, Y., Herskowitz, J. H., Lah, J. J., Ressler, K. J., 2013. AAV2 production with optimized N/P ratio and PEI-mediated transfection results in low toxicity and high titer for in vitro and in vivo applications. J Virol Methods 193, 270-277.

Hurlbut, G. D., Ziegler, R. J., Nietupski, J B., Foley, J. W., Woodworth, L. A., Meyers, E., Bercury, S. D., Pande, N. N., Souza, D. W., Bree, M. P., Lukason, M. J., Marshall, J., Cheng, S. H., Scheule, R. K., 2010. Preexisting immunity and low expression in primates highlight translational challenges for liver-directed AAV8-mediated gene therapy. Mol Ther 18, 1983-1994.

Huttner, N. A., Girod, A., Perabo, L., Edbauer, D., Kleinschmidt, J. A., Buning, H., Hallek, M., 2003. Genetic modifications of the adeno-associated virus type 2 capsid reduce the affinity and the neutralizing effects of human serum antibodies. Gene Ther 10, 2139-2147.

Krissinel, E., Henrick, K., 2007. Inference of macromolecular assemblies from crystalline state. J Mol Biol 372, 774-797.

Kuck, D., Kern, A., Kleinschmidt, J. A., 2007. Development of AAV serotype-specific ELISAs using novel monoclonal antibodies. J Virol Methods 140, 17-24.

Li, C., Narkbunnam, N., Samulski, R. J., Asokan, A., Hu, G., Jacobson, L. J., Manco-Johnson, M. J., Monahan, P. E., 2012. Neutralizing antibodies against adeno-associated virus examined prospectively in pediatric patients with hemophilia. Gene Ther 19, 288-294.

Limberis, M. P., Vandenberghe, L. H., Zhang, L., Pickles, R. J., Wilson, J. M., 2009. Transduction efficiencies of novel AAV vectors in mouse airway epithelium in vivo and human ciliated airway epithelium in vitro. Mol Ther 17, 294-301.

Manno, C. S., Pierce, G. F., Arruda, V. R., Glader, B., Ragni, M., Rasko, J. J., Ozelo, M. C., Hoots, K., Blatt, P., Konkle, B., Dake, M., Kaye, R., Razavi, M., Zajko, A., Zehnder, J., Rustagi, P. K., Nakai, H., Chew, A., Leonard, D., Wright, J. F., Lessard, R. R., Sommer, J. M., Tigges, M., Sabatino, D., Luk, A., Jiang, H., Mingozzi, F., Couto, L., Ertl, H. C., High, K. A., Kay, M. A., 2006. Successful transduction of liver in hemophilia by AAV-Factor IX and limitations imposed by the host immune response. Nat Med 12, 342-347.

McCraw, D. M., O'Donnell, J. K., Taylor, K. A., Stagg, S. M., Chapman, M. S., 2012. Structure of adeno-associated virus-2 in complex with neutralizing monoclonal antibody A20. Virology 431, 40-49.

Mendell, J. R., Rodino-Klapac, L. R., Rosales-Quintero, X., Kota, J., Coley, B. D., Galloway, G., Craenen, J. M., Lewis, S., Malik, V., Shilling, C., Byrne, B. J., Conlon, T., Campbell, K. J., Bremer, W. G., Viollet, L., Walker, C. M., Sahenk, Z., Clark, K. R., 2009. Limb-girdle muscular dystrophy type 2D gene therapy restores alpha-sarcoglycan and associated proteins. Ann Neurol 66, 290-297.

Mietzsch, M., Grasse, S., Zurawski, C., Weger, S., Bennett, A., Agbandje-McKenna, M., Muzyczka, N., Zolotukhin, S., Heilbronn, R., 2014. OneBac: platform for scalable and high-titer production of adeno-associated virus serotype 1-12 vectors for gene therapy. Hum Gene Ther 25, 212-222.

Miller, E. B., Gurda-Whitaker, B., Govindasamy, L., McKenna, R., Zolotukhin, S., Muzyczka, N., Agbandje-McKenna, M., 2006. Production, purification and preliminary X-ray crystallographic studies of adeno-associated virus serotype 1. Acta Crystallogr Sect F Struct Biol Cryst Commun 62, 1271-1274.

Mindell, J. A., Grigorieff, N., 2003. Accurate determination of local defocus and specimen tilt in electron microscopy. J Struct Biol 142, 334-347.

Mori, S., Takeuchi, T., Enomoto, Y., Kondo, K., Sato, K., Ono, F., Sata, T., Kanda, T., 2008. Tissue distribution of cynomolgus adeno-associated viruses AAV10, AAV11, and AAVcy.7 in naturally infected monkeys. Arch Virol 153, 375-380.

Nathwani, A. C., Tuddenham, E. G., Rangarajan, S., Rosales, C., McIntosh, J., Linch, D. C., Chowdary, P., Riddell, A., Pie, A. J., Harrington, C., O'Beirne, J., Smith, K., Pasi, J., Glader, B., Rustagi, P., Ng, C. Y., Kay, M. A., Zhou, J., Spence, Y., Morton, C. L., Allay, J., Coleman, J., Sleep, S., Cunningham, J. M., Srivastava, D., Basner-Tschakarjan, E., Mingozzi, F., High, K. A., Gray, J. T., Reiss, U. M., Nienhuis, A. W., Davidoff, A. M., 2011. Adenovirus-associated virus vector-mediated gene transfer in hemophilia B. N Engl J Med 365, 2357-2365.

Ng, R., Govindasamy, L., Gurda, B. L., McKenna, R., Kozyreva, O. G., Samulski, R. J., Parent, K. N., Baker, T. S., Agbandje-McKenna, M., 2010. Structural characterization of the dual glycan binding adeno-associated virus serotype 6. J Virol 84, 12945-12957.

Pettersen, E. F., Goddard, T. D., Huang, C. C., Couch, G. S., Greenblatt, D. M., Meng, E. C., Ferrin, T. E., 2004. UCSF Chimera—a visualization system for exploratory research and analysis. J Comput Chem 25, 1605-1612.

Rose, J. A., Maizel, J. V., Jr., Inman, J. K., Shatkin, A. J., 1971. Structural proteins of adenovirus-associated viruses. J Virol 8, 766-770.

Schmidt, M., Voutetakis, A., Afione, S., Zheng, C., Mandikian, D., Chiorini, J. A., 2008. Adeno-associated virus type 12 (AAV12): a novel AAV serotype with sialic acid- and heparan sulfate proteoglycan-independent transduction activity. J Virol 82, 1399-1406.

Schrödinger, L., 2017. The PyMOL Molecular Graphics System, Version 2.0.

Snijder, J., van de Waterbeemd, M., Damoc, E., Denisov, E., Grinfeld, D., Bennett, A., Agbandje-McKenna, M., Makarov, A., Heck, A. J., 2014. Defining the stoichiometry and cargo load of viral and bacterial nanoparticles by Orbitrap mass spectrometry. J Am Chem Soc 136, 7295-7299.

Sonntag, F., Kother, K., Schmidt, K., Weghofer, M., Raupp, C., Nieto, K., Kuck, A., Gerlach, B., Bottcher, B., Muller, O. J., Lux, K., Horer, M., Kleinschmidt, J. A., 2011. The assembly-activating protein promotes capsid assembly of different adeno-associated virus serotypes. J Virol 85, 12686-12697.

Tseng, Y. S., Agbandje-McKenna, M., 2014. Mapping the AAV Capsid Host Antibody Response toward the Development of Second Generation Gene Delivery Vectors. Front Immunol 5, 9.

Tseng, Y. S., Gurda, B. L., Chipman, P., McKenna, R., Afione, S., Chiorini, J. A., Muzyczka, N., Olson, N. H., Baker, T. S., Kleinschmidt, J., Agbandje-McKenna, M., 2015. Adeno-associated virus serotype 1 (AAV1)- and AAV5-antibody complex structures reveal evolutionary commonalities in parvovirus antigenic reactivity. J Virol 89, 1794-1808.

Tseng, Y. S., Vliet, K. V., Rao, L., McKenna, R., Byrne, B. J., Asokan, A., Agbandje-McKenna, M., 2016. Generation and characterization of anti-Adeno-associated virus serotype 8 (AAV8) and anti-AAV9 monoclonal antibodies. J Virol Methods 236, 105-110.

van Heel, M., Schatz, M., 2005. Fourier shell correlation threshold criteria. J Struct Biol 151, 250-262.

Wagner, J. A., Messner, A. H., Moran, M. L., Daifuku, R., Kouyama, K., Desch, J. K., Manley, S., Norbash, A. M., Conrad, C. K., Friborg, S., Reynolds, T., Guggino, W. B., Moss, R. B., Carter, B. J., Wine, J. J., Flotte, T. R., Gardner, P., 1999. Safety and biological efficacy of an adeno-associated virus vector-cystic fibrosis transmembrane regulator (AAV-CFTR) in the cystic fibrosis maxillary sinus. Laryngoscope 109, 266-274.

Wobus, C. E., Hugle-Dorr, B., Girod, A., Petersen, G., Hallek, M., Kleinschmidt, J. A., 2000. Monoclonal antibodies against the adeno-associated virus type 2 (AAV-2) capsid: epitope mapping and identification of capsid domains involved in AAV-2-cell interaction and neutralization of AAV-2 infection. J Virol 74, 9281-9293.

Wu, Z., Asokan, A., Grieger, J. C., Govindasamy, L., Agbandje-McKenna, M., Samulski, R. J., 2006. Single amino acid changes can influence titer, heparin binding, and tissue tropism in different adeno-associated virus serotypes. J Virol 80, 11393-11397.

Xiao, C., Rossmann, M. G., 2007. Interpretation of electron density with stereographic roadmap projections. J Struct Biol 158, 182-187.

Yan, X., Dryden, K. A., Tang, J., Baker, T. S., 2007a. Ab initio random model method facilitates 3D reconstruction of icosahedral particles. J Struct Biol 157, 211-225.

Yan, X., Sinkovits, R. S., Baker, T. S., 2007b. AUTO3DEM—an automated and high throughput program for image reconstruction of icosahedral particles. J Struct Biol 157, 73-82.

Zadori, Z., Szelei, J., Lacoste, M. C., Li, Y., Gariepy, S., Raymond, P., Allaire, M., Nabi, I. R., Tijssen, P., 2001. A viral phospholipase A2 is required for parvovirus infectivity. Dev Cell 1, 291-302.

Zolotukhin, S., Potter, M., Zolotukhin, I., Sakai, Y., Loiler, S., Fraites, T. J., Chiodo, V. A., Phillipsberg, T., Muzyczka, N., Hauswirth, W. W., Flotte, T. R., Byrne, B. J., Snyder, R. O., 2002. Production and purification of serotype 1, 2, and 5 recombinant adeno-associated viral vectors. Methods 28, 158-167.

---

What is claimed is:

1. A method comprising:

administering to a subject a recombinant AAV6 (rAAV6) particle comprising an AAV6 capsid protein having a single substitution consisting of a substituted amino acid at position 531, wherein the substituted amino acid at position 531 is glutamic acid (E), aspartic acid (D), histidine (H), tyrosine (Y), methionine (M), or leucine (L), wherein the rAAV6 particle comprises a gene of interest, wherein the subject is seropositive for an adeno-associated virus (AAV) capsid protein of serotype 6 (AAV6) antigen comprising lysine 531, and wherein the subject is not seropositive for the capsid protein comprising the substituted amino acid.

2. The method of claim 1, wherein the subject is human.

3. The method of claim 1, wherein the method further comprises determining the subject has anti-AAV6 antibodies that bind to the AAV6 antigen comprising lysine 531.

4. The method of claim 3, wherein determining the subject has anti-AAV6 antibodies comprises:

incubating a sample of serum obtained from the subject with one or more AAV6 capsid antigens, and measuring the amount of anti-AAV6 antibodies bound to the one or more AAV6 capsid antigens, wherein the one or more AAV6 capsid antigens are bound to a solid support.

5. The method of claim 4, wherein the AAV6 capsid antigen is a protein or peptide, wherein the protein or peptide has a sequence that is comprised in AAV6 VP1, VP2 or VP3 capsid protein.

6. The method of claim 1, wherein the subject was previously exposed to a rAAV particle and/or had been previously administered a rAAV particle.

7. The method of claim 1, wherein the gene of interest encodes a therapeutic protein, an antibody, a peptibody, a growth factor, a clotting factor, a hormone, a membrane protein, a cytokine, a chemokine, an activating or inhibitory peptide acting on cell surface receptors or ion channels, a cell-permeant peptide targeting intracellular processes, a thrombolytic, an enzyme, a bone morphogenetic protein, a differentiation factor, a nuclease or other protein used for gene editing, an Fc-fusion protein, an anticoagulant, a nuclease, guide RNA or other nucleic acid or protein for gene editing.

8. The method of claim 1, wherein the rAAV6 particle is administered to the subject subcutaneously, intraocularly, intravitreally, subretinally, parenterally, intravenously (IV), intracerebro-ventricularly, intramuscularly, intrathecally (IT), intracisternally, orally, intraperitoneally, by oral or nasal inhalation, or by direct injection to one or more cells, tissues, or organs by direct injection.

9. A method comprising:

administering to a subject a subsequent rAAV6 particle, wherein the subsequent rAAV6 particle comprises an AAV6 capsid protein having a single substitution consisting of a substituted amino acid at position 531, wherein the substituted amino acid at position 531 is glutamic acid (E), aspartic acid (D), histidine (H), tyrosine (Y), methionine (M), or leucine (L), wherein the subject had previously received a recombinant AAV (rAAV) particle comprising an AAV6 capsid protein that comprises lysine at position 531, wherein the subsequent rAAV6 particle comprises a gene of interest, wherein the subject is seropositive for an adeno-associated virus (AAV) capsid protein of serotype 6 (AAV6) antigen comprising lysine 531 and the subject is not seropositive for the capsid protein comprising the substituted amino acid.

10. The method of claim 9, wherein the subject is human.

11. The method of claim 9, wherein the method further comprises determining the subject has anti-AAV6 antibodies that bind to the AAV6 antigen comprising lysine 531.

12. The method of claim 11, wherein determining the subject has anti-AAV6 antibodies comprises:

incubating a sample of serum obtained from the subject with one or more AAV6 capsid antigens, and measuring the amount of anti-AAV6 antibodies bound to the one or more AAV6 capsid antigens, wherein the one or more AAV6 capsid antigens are bound to a solid support.

13. The method of claim 12, wherein the AAV6 capsid antigen is a protein or peptide, wherein the protein or peptide has a sequence that is comprised in an AAV6 VP1, VP2 or VP3 capsid protein.

14. The method of claim 9, wherein the gene of interest encodes a therapeutic protein, an antibody, a peptibody, a growth factor, a clotting factor, a hormone, a membrane protein, a cytokine, a chemokine, an activating or inhibitory peptide acting on cell surface receptors or ion channels, a cell-permeant peptide targeting intracellular processes, a thrombolytic, an enzyme, a bone morphogenetic protein, a differentiation factor, a nuclease or other protein used for gene editing, an Fc-fusion protein, an anticoagulant, a nuclease, guide RNA or other nucleic acid or protein for gene editing.

15. A recombinant AAV6 (rAAV6) capsid protein comprising one of the following amino acids at position 531 according to SEQ ID NO: 1: histidine (H), methionine (M), or leucine (L).

16. The method of claim 1, wherein the substituted amino acid at position 531 is glutamic acid, aspartic acid, histidine, or tyrosine.

17. The method of claim 1, wherein the substituted amino acid at position 531 is negatively charged.

18. The method of claim 9, wherein the substituted amino acid at position 531 is glutamic acid, aspartic acid, histidine, or tyrosine.

19. The method of claim 9, wherein the substituted amino acid at position 531 is negatively charged.

* * * * *

SEQUENCE LISTING

<160> NUMBER OF SEQ ID NOS: 1

<210> SEQ ID NO 1
<211> LENGTH: 736
<212> TYPE: PRT
<213> ORGANISM: Artificial Sequence
<220> FEATURE:
<223> OTHER INFORMATION: Synthetic polypeptide

<400> SEQUENCE: 1

-continued

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
                260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
                340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
```

-continued

```
                420                   425                   430
Arg Leu Met Asn Pro Leu Ile Asp Gln Tyr Leu Tyr Tyr Leu Asn Arg
        435                   440                   445

Thr Gln Asn Gln Ser Gly Ser Ala Gln Asn Lys Asp Leu Leu Phe Ser
        450                   455                   460

Arg Gly Ser Pro Ala Gly Met Ser Val Gln Pro Lys Asn Trp Leu Pro
465                   470                   475                   480

Gly Pro Cys Tyr Arg Gln Gln Arg Val Ser Lys Thr Lys Thr Asp Asn
                485                   490                   495

Asn Asn Ser Asn Phe Thr Trp Thr Gly Ala Ser Lys Tyr Asn Leu Asn
                500                   505                   510

Gly Arg Glu Ser Ile Ile Asn Pro Gly Thr Ala Met Ala Ser His Lys
        515                   520                   525

Asp Asp Lys Asp Lys Phe Phe Pro Met Ser Gly Val Met Ile Phe Gly
        530                   535                   540

Lys Glu Ser Ala Gly Ala Ser Asn Thr Ala Leu Asp Asn Val Met Ile
545                   550                   555                   560

Thr Asp Glu Glu Glu Ile Lys Ala Thr Asn Pro Val Ala Thr Glu Arg
                565                   570                   575

Phe Gly Thr Val Ala Val Asn Leu Gln Ser Ser Ser Thr Asp Pro Ala
                580                   585                   590

Thr Gly Asp Val His Val Met Gly Ala Leu Pro Gly Met Val Trp Gln
        595                   600                   605

Asp Arg Asp Val Tyr Leu Gln Gly Pro Ile Trp Ala Lys Ile Pro His
        610                   615                   620

Thr Asp Gly His Phe His Pro Ser Pro Leu Met Gly Gly Phe Gly Leu
625                   630                   635                   640

Lys His Pro Pro Pro Gln Ile Leu Ile Lys Asn Thr Pro Val Pro Ala
                645                   650                   655

Asn Pro Pro Ala Glu Phe Ser Ala Thr Lys Phe Ala Ser Phe Ile Thr
                660                   665                   670

Gln Tyr Ser Thr Gly Gln Val Ser Val Glu Ile Glu Trp Glu Leu Gln
        675                   680                   685

Lys Glu Asn Ser Lys Arg Trp Asn Pro Glu Val Gln Tyr Thr Ser Asn
        690                   695                   700

Tyr Ala Lys Ser Ala Asn Val Asp Phe Thr Val Asp Asn Asn Gly Leu
705                   710                   715                   720

Tyr Thr Glu Pro Arg Pro Ile Gly Thr Arg Tyr Leu Thr Arg Pro Leu
                725                   730                   735
```